(12) United States Patent
Kim et al.

(10) Patent No.: US 7,022,850 B2
(45) Date of Patent: Apr. 4, 2006

(54) BICYCLICPYRIMIDONES AND THEIR USE TO TREAT DISEASES

(75) Inventors: Kyoung S. Kim, North Brunswick, NJ (US); Songfeng Lu, Raritan, NJ (US); X. Christopher Sheng, Foster City, CA (US); Alvin Donald Crews, Voorhees, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 10/848,089

(22) Filed: May 18, 2004

(65) Prior Publication Data

US 2004/0242596 A1 Dec. 2, 2004

Related U.S. Application Data

(60) Provisional application No. 60/472,880, filed on May 22, 2003.

(51) Int. Cl.
*C07D 498/04* (2006.01)
*C07D 513/04* (2006.01)

(52) U.S. Cl. .................................. 544/255; 544/256
(58) Field of Classification Search ............ 514/260.1, 514/262.1; 544/255, 256
See application file for complete search history.

(56) References Cited

FOREIGN PATENT DOCUMENTS

| WO | WO 96/22991 | 8/1996 |
|---|---|---|
| WO | WO 97/33890 | 9/1997 |
| WO | WO 00/39131 | 7/2000 |
| WO | WO 03/049527 A2 | 6/2003 |
| WO | WO 2003049527 A2 * | 6/2004 |
| WO | WO 2004/78758 | 9/2004 |

OTHER PUBLICATIONS

Qun Li; Hing L Sham, Expert Opinion on Therapeutic Patents, 2002, vol. 12, No. 11, pp. 1663-1702.*
Paul J Coleman; Mark E Fraley, Expert Opinion on Therapeutic Patents, 2004, vol. 14, No. 12, pp. 1659-1667.*
ClinicalTrials.gov "Identifier NCT00095628", National Institutes of Health, [online] May 4, 2005, [retrieved on May 20, 2005]. Retrieved from the internet, <http://www.clinicaltrials.gov/ct/gui/show/NCT00095628>.*
Draetta, G. and Pagano, M. in "Annual Reports in Medicinal Chemistry, vol. 31", 1996, Academic Press, San Diego, p 241-246.*

* cited by examiner

*Primary Examiner*—Thomas C. McKenzie
(74) *Attorney, Agent, or Firm*—Maureen S. Gibbons

(57) ABSTRACT

The present invention is directed to dihydropyrimidones having formula I or II and methods of using them to induce mitotic arrest, thereby making them useful as anti-cancer agents and other diseases that can be treated by inducing mitotic arrest.

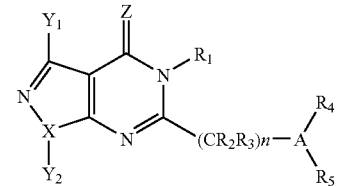

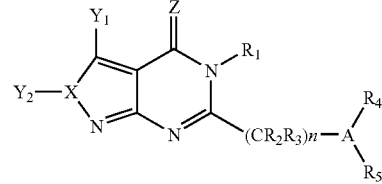

16 Claims, No Drawings

BICYCLICPYRIMIDONES AND THEIR USE TO TREAT DISEASES

RELATED APPLICATIONS

This application claims priority benefit under Title 35 § 119 (e) of U.S. provisional Application No. 60/472,880, filed May 22, 2003, the contents of which are herein incorporated by reference.

FIELD OF THE INVENTION

This invention relates to novel compounds that interrupt mitosis thereby making the compounds useful for the treatment of proliferative diseases, such as cancer.

BACKGROUND OF THE INVENTION

Cell proliferation and programmed cell death play important roles in the growth and development of an organism. In proliferative diseases such as cancer, the processes of cell proliferation and/or programmed cell death are often perturbed. For example, a cancer cell may have unregulated cell division through either the overexpression of a positive regulator of the cell cycle or the loss of a negative regulator of the cell cycle, perhaps by mutation. Alternatively, a cancer cell may have lost the ability to undergo programmed cell death through the overexpression of a negative regulator of apoptosis. Hence, there is a need to develop new chemotherapeutic drugs that will restore the processes of checkpoint control and programmed cell death to cancerous cells.

One approach to the treatment of human cancers is to target a protein that is essential for cell cycle progression. In order for the cell cycle to proceed from one phase to the next, certain prerequisite events must be completed. There are checkpoints within the cell cycle that enforce the proper order of events and phases. One such checkpoint is the spindle checkpoint that occurs during the metaphase stage of mitosis. Small molecules that target proteins with essential functions in mitosis may initiate the spindle checkpoint to arrest cells in mitosis. Of the small molecules that arrest cells in mitosis, those which display anti-tumor activity in the clinic also induce apoptosis, the morphological changes associated with programmed cell death. An effective chemotherapeutic for the treatment of cancer may be one that induces checkpoint control and subsequent programmed cell death.

Most compounds known to cause mitotic arrest and apoptosis act as tubulin binding agents. These compounds alter the dynamic instability of microtubules and indirectly alter the function/structure of the mitotic spindle thereby causing mitotic arrest. Because most of these compounds target the tubulin protein, a component of all microtubules, they may also affect normal cellular processes in which microtubules have a role. Hence, a need exists for small molecules that specifically target proteins associated with proliferating cells, such as Eg5.

Eg5 is one of several kinesin-like motor proteins that are localized to the mitotic spindle and known to be required for formation and/or function of the bipolar mitotic spindle. Recently, there was a report of a small molecule that disturbs bipolarity of the mitotic spindle (Mayer, T. U. et. al. 1999. Science 286(5441) 971–4). More specifically, the small molecule induced the formation of an aberrant mitotic spindle wherein a monoastral array of microtubules emanated from a central pair of centrosomes, with chromosomes attached to the distal ends of the microtubules. The small molecule was dubbed "monastrol" after the monoastral array. This monoastral array phenotype had been previously observed in mitotic cells that were immunodepleted of the Eg5 motor protein.

The distinctive monoastral array phenotype facilitated identification of monastrol as a potential inhibitor of Eg5. Indeed, monastrol was further shown to inhibit the Eg5 motor-driven motility of microtubules in an in vitro assay. Furthermore, monastrol had no apparent effect upon the related kinesin motor or upon the motor(s) responsible for golgi apparatus movement within the cell. Cells that display the monoastral array phenotype, either through immunodepletion of Eg5 or monastrol inhibition of Eg5, arrest in M-phase of the cell cycle. Unfortunately, however, the mitotic arrest induced by either of these mechanisms is transient. (Kapoor, 2000. *J. Cell. Biol.* 150(5) 975–80). Both the monoastral array phenotype and the monastrol induced cell cycle arrest in mitosis are reversible. Cells recover to form a normal bipolar mitotic spindle, to complete mitosis, and to proceed through the cell cycle and normal cell proliferation. This suggests that a small molecule inhibitor of Eg5 that induced a transient mitotic arrest may not be effective for the treatment of cancer cell proliferation. Nonetheless, the discovery that monastrol causes mitotic arrest is intriguing and hence there is a need to further study and identify compounds that can be used to modulate the Eg5 motor protein in a manner that would be effective in the treatment of human cancers. There is also a need to explore the use of these compounds in combination with other antineoplastic agents.

SUMMARY

The compounds of the invention cause the interruption of mitosis, and as such, can be used to treat proliferative diseases. For example, the compounds of the instant invention can be used as antiproliferatives and anticancer agents. More specifically, the invention comprises compounds having formula I or II

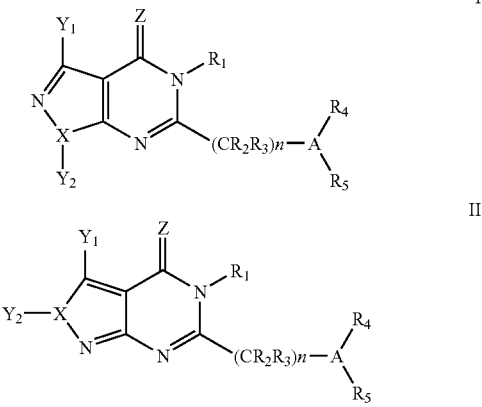

wherein:
X is O, S or N, provided that if X is O or S, $Y_2$ is absent;
$Y_1$ is H, alkyl, substituted alkyl, aryl, substituted aryl, cycloalkyl or substituted cycloalkyl;
$Y_2$ is absent, H or alkyl;
Z is O or S;
$R_1$ is H, alkyl, substituted alkyl, aryl, substituted aryl, aralkyl, or heteroarylalkyl;

$R_2$ and $R_3$ are, independently, H, alkyl, cycloalkyl or halogen or $R_2$ and $R_3$ may be taken together to form a $C_3$ to $C_7$ cycloalkyl;

n is 1 or 2;

A is N;

$R_4$ is $C(=O)R_9$, $C(=O)OR_{10}$, $C(=O)NR_{11}R_{12}$, $S(O)_2R_{13}$, alkyl, substituted alkyl, aryl, substituted aryl or aralkyl;

$R_9$, $R_{10}$, $R_{11}$, $R_{12}$, $R_{13}$ are independently H, alkyl, substituted alkyl, cycloalkyl, substituted cycloalkyl, aryl, substituted aryl, heteroaryl, or substituted heteroaryl; and $R_5$ is H, alkyl, substituted alkyl, cycloalkyl, substituted cycloalkyl, aryl, substituted aryl, heteroaryl, or substituted heteroaryl.

The present invention also provides methods of inducing cytotoxicity comprising administering to a mammal in need of such treatment an effective amount of the compounds of the present invention.

The present invention also provides methods for treating a proliferative disease, such as cancer, via modulation of the Eg5 motor protein comprising administering to a mammal need of such treatment an effective amount of the compound of the present invention, as defined above.

DETAILED DESCRIPTION OF THE INVENTION

The present invention provides for compounds having Formula I or II, as defined above, pharmaceutical compositions employing such compounds, and methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. An alkyl group is an optionally substituted straight, branched or cyclic saturated hydrocarbon group. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as $CCl_3$ or $CF_3$), alkoxy, alkylthio, hydroxy, cyano, carboxy (—COOH), alkyloxycarbonyl (—C(O)OR), alkylcarbonyloxy (—OCOR), amino (—$NH_2$), amido, carbamoyl (—NHCOOR— or —OCONHR—), urea (—NHCONHR—) or thiol (—SH).

The term "alkenyl" herein alone or as part of another group refers to a hydrocarbon radical straight, branched or cyclic containing from 2 to 12 carbon atoms and at least one carbon to carbon double bond. Alkenyl groups may also be substituted at any available point of attachment. Exemplary substituents for alkenyl groups include those listed above for alkyl groups.

The term "alkynyl" herein alone or as part of another group refers to a hydrocarbon radical straight, branched or cyclic containing from 2 to 12 carbon atoms and at least one carbon to carbon triple bond. Alkynyl groups may also be substituted at any available point of attachment. Exemplary substituents for alkenyl groups include those listed above for alkyl groups.

The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

The term "cycloalkyl" herein alone or as part of another group is a species of alkyl containing from 3 to 15 carbon atoms, without alternating or resonating double bonds between carbon atoms. It may contain from 1 to 4 rings. Exemplary groups include cyclopropyl, cyclobutyl, cyclopentyl, cyclohexyl, adamantyl, etc. Cycloalkyl groups may be substituted at any available point of attachment. Exemplary substituents include one or more of the following groups: halogen, alkyl, alkoxy, alkyl hydroxy, amino, nitro, cyano, thiol and/or alkylthio, and any of the substitituents described above for alkyl groups.

The terms "alkoxy" or "alkylthio" herein alone or as part of another group denote an alkyl group as described above bonded through an oxygen linkage (—O—) or a sulfur linkage (—S—), respectively.

The term "alkyloxycarbonyl" herein alone or as part of another group denotes an alkoxy group bonded through a carbonyl group. An alkoxycarbonyl radical is represented by the formula: —C(O)OR, where the R group is a straight or branched $C_{1-6}$ alkyl group, cycloalkyl, aryl, or heteroaryl.

The term "alkylcarbonyl" herein alone or as part of another group refers to an alkyl group bonded through a carbonyl group.

The term "aminocarbonyl" herein alone or as part of another group refers to an amino group bonded through a carbonyl group.

The term "alkoxyalkyl" herein alone or as part of another group refers to an alkoxy group bonded through an alkyl group.

The term "alkoxycarbonyl" herein alone or as part of another group refers to an alkoxy group bonded through a carbonyl group.

The term "alkylcarbonyloxy" herein alone or as part of another group denotes an alkylcarbonyl group bonded through an oxygen linkage.

The term "amino" herein alone or as part of another group refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, or any of the alkyl or aryl substituents set out herein. In some embodiments, the amino groups are substituted with carboxyl or carbonyl to form N-acyl or N-carbamoyl derivatives The term "aralkyl" herein alone or as part of another group denotes an aromatic ring bonded through an alkyl group as described above wherein the aromatic ring may be substituted as described below.

The term "heteroarylalkyl" herein alone or as part of another group denotes a heteroaryl group that is bonded through an alkyl group. The heteroaryl group may be substituted as described below.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Preferred aryl groups include phenyl and naphthalene groups. Aryl groups may optionally be substituted with one or more groups including, but not limited to halogen, alkyl, alkoxy, hydroxy, carboxy, carbamoyl, alkyloxycarbonyl, nitro, alkenyloxy, trifluoromethyl, amino, cycloalkyl, aryl, heteroaryl, cyano, alkyl S(O)$_m$R (m=O, 1, 2), such as S(O)$_2$F, or thiol.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings and are known in the art. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —CO$_2$H, —C(=O)H, —CO$_2$-alkyl, —C(=O)alkyl, phenyl, benzyl, phenylethyl, phenyloxy, phenylthio, cycloalkyl, substituted cycloalkyl, heterocyclo, heteroaryl,—NR'R", —C(=O)NR'R", —CO$_2$NR'R", —C(=O)NR'R", —NR'CO$_2$'R", —NR'C(=O)R", —SO$_2$NR'R", and —NR'SO$_2$'R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocycloalkyl" herein alone or as part of another group refers to a cycloalkyl group (nonaromatic) in which one of the carbon atoms in the ring is replaced by a heteroatom selected from O, S or N, and in which up to three additional carbon atoms may be replaced by said heteroatoms. The heterocycloalkyl may be optionally substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino),cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclic rings are piperidyl, morpholinyl, piperazinyl. The heterocyclic ring may be attached to the parent structure through a carbon atom or through any heteroatom of the heterocyclyl that results in a stable structure.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

As used herein, the term "mammal" encompasses all mammalian species.

The term "anticancer" agent includes any known agent that is useful for the treatment of cancer including 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, chlorotrianisene, Hydroxyprogesterone, Aminoglutethimide, Estramustine, Medroxyprogesteroneacetate, Leuprolide, Flutamide, Toremifene, Zoladex, matrix metalloproteinase inhibitors, VEGF inhibitors, including as anti-VEGF antibodies such as Avastin, and small molecules such as ZD6474 and SU6668, vatalanib, BAY-43-9006, SU11248, CP-547632, and CEP-7055 are also included. Anti-Her2 antibodies from Genentech (such as Herceptin) may also be utilized. Suitable EGFR inhibitors include gefitinib, erlotinib, and cetuximab. Pan Her inhibitors include canertinib, EKB-569, and GW-572016. Also included are Src inhibitors as well as Casodex® (bicalutamide, Astra Zeneca), Tamoxifen, MEK-1 kinase inhibitors, MAPK kinase inhibitors, PI3 inhibitors, and PDGF inhibitors, such as imatinib. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kinases, and inhibitors of integrin signaling. Additional anticancer agents include microtubule-stabilizing agents such as paclitaxel (also known as Taxol®), docetaxel (also known as Taxotere®), 7-O-methylthiomethylpaclitaxel (disclosed in U.S. Pat. No. 5,646,176), 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Ser. No. 09/712,352 filed on Nov. 14, 2000), C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (disclosed in WO 99/02514), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione (disclosed in U.S. Pat. No. 6,262,094) and derivatives thereof; and microtubule-disruptor agents. Also suitable are CDK inhibitors, an antiproliferative cell cycle inhibitor, epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Additional cytotoxic agents include, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins.

Suitable examples of salts of the compounds according to the invention with inorganic or organic acids are hydrochloride, hydrobromide, sulfate, methanesulfonate, maleate, fumarate, and phosphate. Salts which are unsuitable for pharmaceutical uses but which can be employed, for example, for the isolation or purification of free compounds I or II or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

It should be understood that the present invention includes prodrug forms of the compounds of the present invention. Various forms of prodrugs are well known in the art. For examples of such prodrug derivatives, see: (a) Design of Prodrugs, edited by H. Bundgaard (Elsevier, 1985); and Methods in Enzymology, Vol. 112, pp. 309–396, edited by K. Widder et al., (Academic Press, 1985); (b) A Textbook of Drug Design and Development, edited by Krosgaard-Larsen and H. Bundgaard, Chapter 5, "Design and Application of Prodrugs," by H. Bundgaard, pp. 113–191 (1991); (c) H. Bundgaard, Advanced Drug Delivery Reviews, 8, pp. 1–38 (1992); (d) H. Bundgaard et al., Journal of Pharmaceutical Sciences, 77, 285 (1988); and (e) N. Kayeka et al., Chem. Phar. Bull., 32, 692 (1984).

In general, the instant invention comprises a compound having Formula I or II:

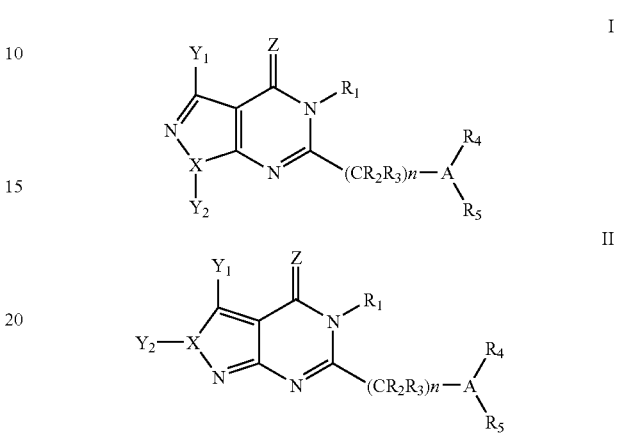

their enantiomers, diastereomers, pharmaceutically acceptable salts, prodrugs and solvates thereof, wherein:

X is O, S or N, provided that if X is O or S, $Y_2$ is absent;

$Y_1$ is H, alkyl, substituted alkyl, aryl, substituted aryl, cycloalkyl or substituted cycloalkyl;

$Y_2$ is absent, H or alkyl;

Z is O or S;

$R_1$ is H, alkyl, substituted alkyl, aryl, substituted aryl, aralkyl, or heteroarylalkyl;

$R_2$ and $R_3$ are, independently, H, alkyl, cycloalkyl or halogen or $R_2$ and $R_3$ may be taken together to form a $C_3$ to $C_7$ cycloalkyl;

n is 1 or 2;

A is N;

$R_4$ is C(=O)$R_9$, C(=O)O$R_{10}$, C(=O)N$R_{11}R_{12}$, S(O)$_2$$R_{13}$, alkyl, substituted alkyl, aryl, substituted aryl or aralkyl;

$R_9$, $R_{10}$, $R_{11}$, $R_{12}$, $R_{13}$ are independently H, alkyl, substituted alkyl, cycloalkyl, substituted cycloalkyl, aryl, substituted aryl, heteroaryl, or substituted heteroaryl; and $R_5$ is H, alkyl, substituted alkyl, cycloalkyl, substituted cycloalkyl, aryl, substituted aryl, heteroaryl, or substituted heteroaryl.

In some preferred embodiments of the present invention, $R_1$ is an aralkyl, such as benzyl.

According to some embodiments, $R_2$ is an alkyl. Preferably a lower alkyl, such as ethyl.

In some embodiments of the present invention, $R_4$ is H, —(C=O)$R_9$, SO$_2R_{13}$ or a substituted alkyl group. Preferred $R_9$ groups include substituted and unsubstituted phenyl groups.

In some embodiments of the present invention, $R_5$ is a substituted alkyl group such as ethyl, propyl, or butyl. Preferred substituents include cyano, amido, or amino groups.

According to some embodiments of the present invention, $Y_1$ is alkyl, substituted alkyl, aryl or substituted aryl.

In one embodiment of the present invention, X is O, S, or N; Z is O; $R_1$ is aralkyl; $R_2$ is alkyl; $R_3$ is H; $R_4$ is H;

—(C=O)R$_9$, —SO$_2$R$_{13}$ or substituted alkyl; R$_5$ is substituted alkyl; and Y$_1$ is alkyl, substituted alkyl, aryl or substituted aryl.

In some preferred embodiments of the present invention, R$_5$ is cyanoethyl, propionamide or propylamine.

The invention further provides a pharmaceutical composition comprising a compound of the present invention, as defined above, and a pharmaceutically acceptable carrier. Optionally the pharmaceutical composition may further comprise at least one other anti-cancer agent formulated as a fixed dose.

The invention also provides a method for treating a proliferative disease, such as cancer, via modulation of the Eg5 motor protein, and/or, inducing apoptosis comprising administering to a mammalian species in need of such treatment an effective amount of a compound of the present invention. These methods may further include administration of at least one other anticancer agent, simultaneously or sequentially.

Certain compounds of the present invention may generally be prepared according to the following schemes and the knowledge of one skilled in the art. Solvates (e.g., hydrates) of the compounds of the present invention are also within the scope of the present invention, and methods of solvation are generally known in the art. Accordingly, the compounds of the instant invention may be in the free or solvate form, and may be obtained by methods exemplified by the following schemes.

Appropriately substituted malononitrile 1 starting materials, available from Aldrich Chemical Co., may be reacted with hydroxyl amine to generate substituted isoxazole 2, which can be condensed with various anhydrides to obtain isoxazolodihydropyrimidinone 3 (See, U.S. Pat. No. 3,679,682, herein incorporated by reference.) Alkylation of isoxazolodihydropyrimidinone 3 with R$_1$X followed by bromination afforded bromo compound 5. Amination with alkyl amine and acylation provided final isoxazolodihydropyrimidinone analogues of the present invention.

SCHEME 1

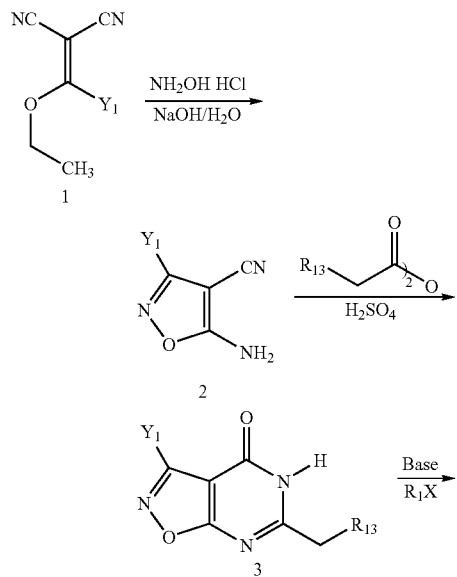

Alternatively, analogues substituted at C-5 by various Y$_1$ groups may be prepared starting with appropriately substituted halo oximes as shown in Scheme 2 (Y$_1$=CF$_3$). Treatment of the bromooxime with cyanoacetamide provides the C-5 substituted isoxazole (See, U.S. Pat. No. 3,679,682; J. Heterocyclic Chem. 1535 (1986), the disclosures of which are herein incorporated by reference) which may be reacted with C-2 amino substituted ester to form an isoxazolodihydropyrimidinone 8. Alkylation at N-3 followed by deprotection and reductive alkylation can provide isoxazolopyrimidine 11. Acylation followed by deprotection can afford the final isoxazolodihydropyrimidinone analogue 13.

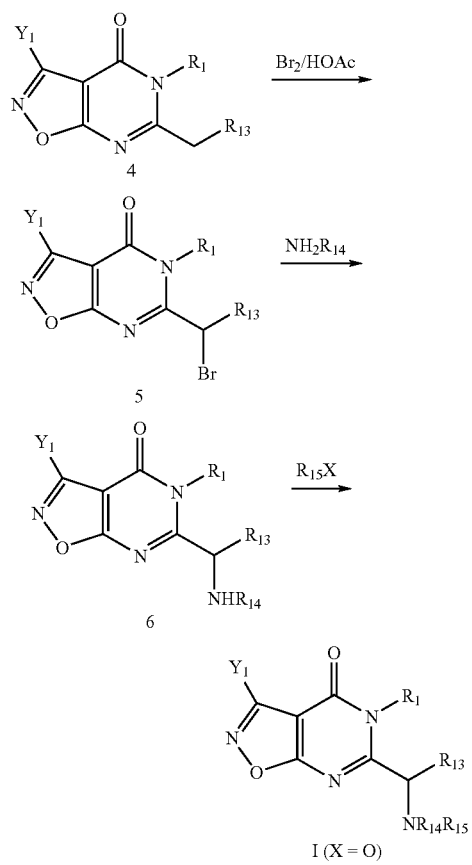

SCHEME 2

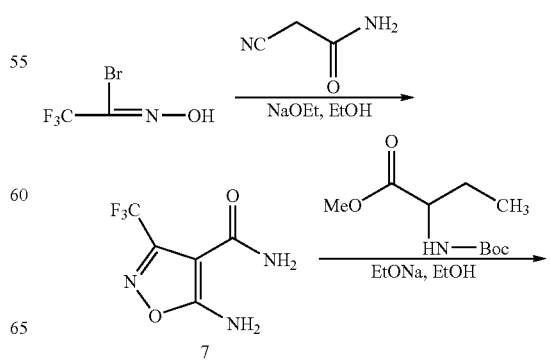

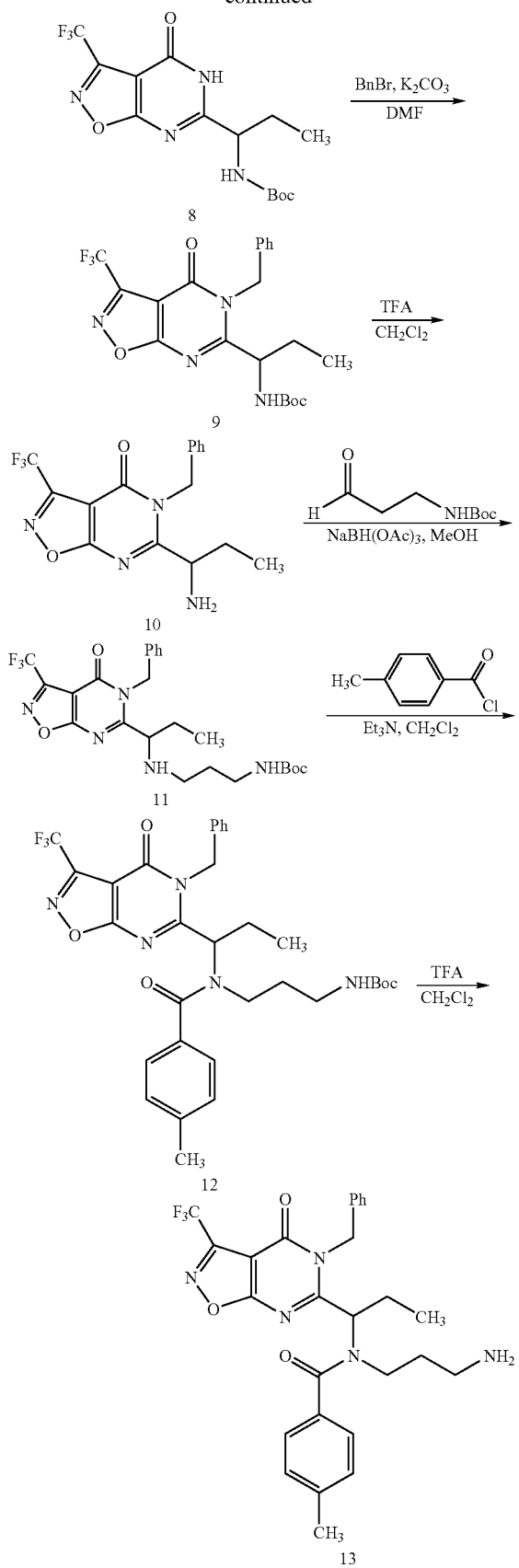

Pyrazolepyrimidine analogues (X=N) may be prepared from pyrazole 14 which can be obtained by reacting ethylenedinitrile with methylhydrazine (Scheme 3). Condensation of this aminocyanopyrazole intermediate with appropriate anhydride can provide pyrazolodihydropyrimidinone 15. Alkylation of N-3 with various alkyl halides followed by bromination and amination with substituted amines can generate pyrazolodihydropyrimidinone 18. Acylation, deprotection and hydrochloride salt formation provides the final analogue of pyrazolodihydropyrimidinone 20 as a HCl salt.

SCHEME 3

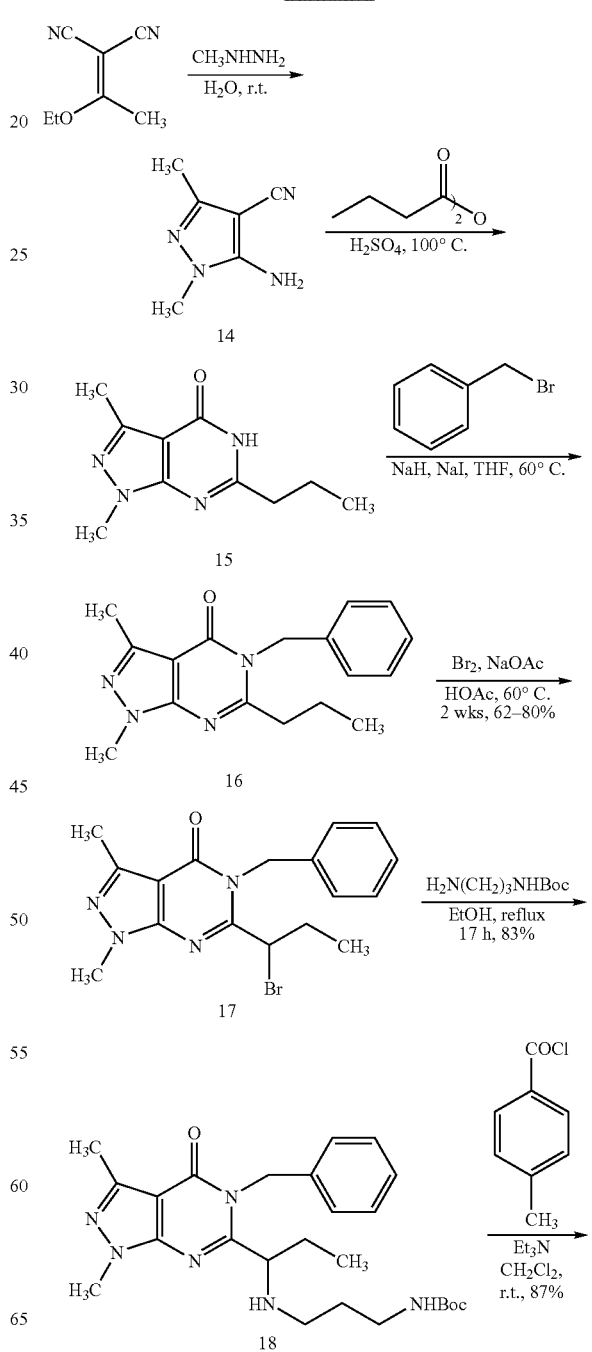

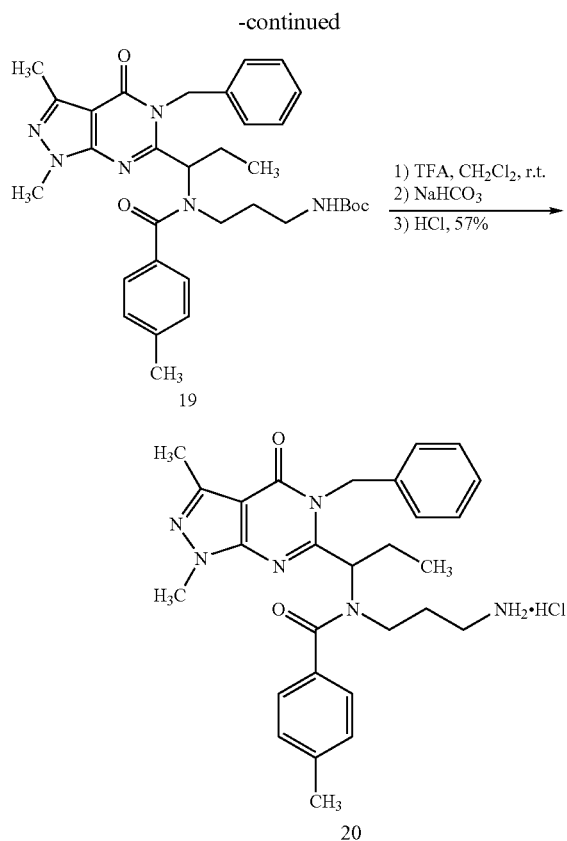
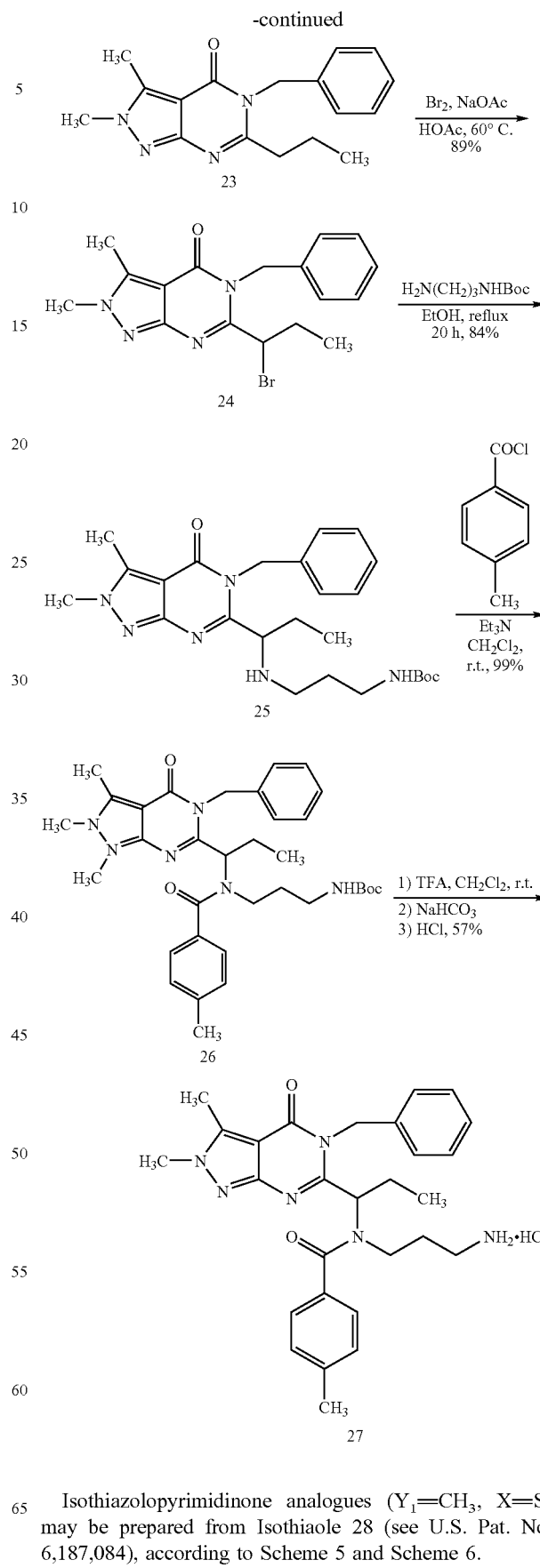

Pyrazolepyrimidine analogues ($Y_1=Y_2=CH_3$) with 2,3-substituents may be prepared from pyrazole 21 which can be obtained by reacting ethylenedinitrile with methylhydrazine in the presence of aqueous sodium hydroxide and following the similar procedures as described before (Scheme 4).

SCHEME 4

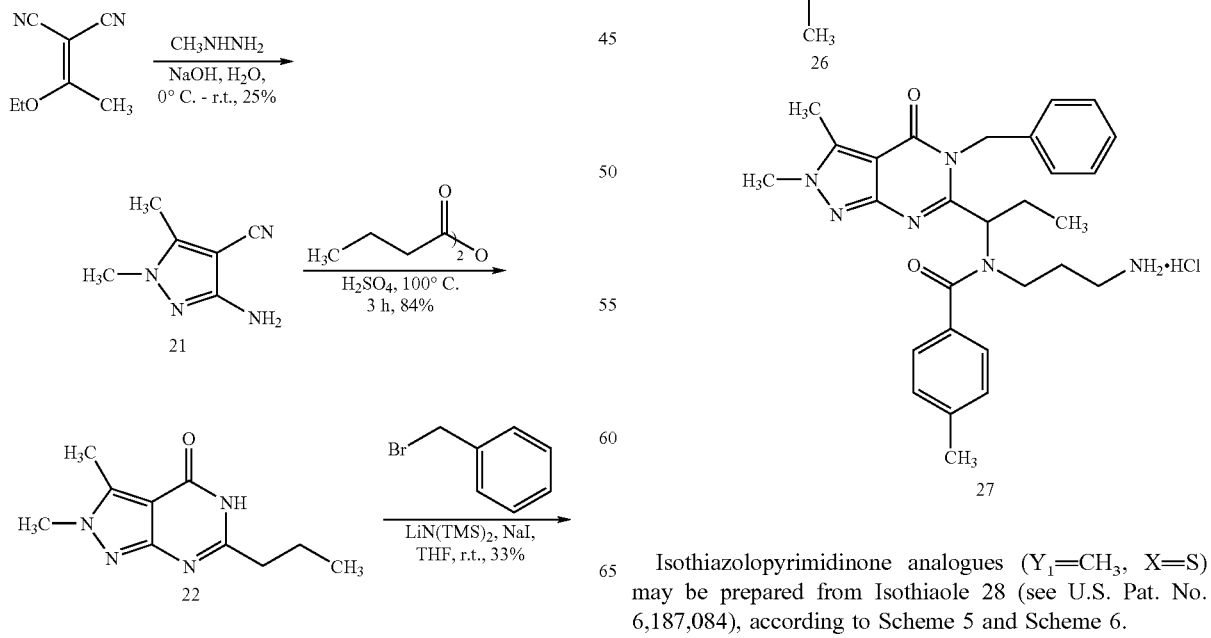

Isothiazolopyrimidinone analogues ($Y_1=CH_3$, $X=S$) may be prepared from Isothiaole 28 (see U.S. Pat. No. 6,187,084), according to Scheme 5 and Scheme 6.

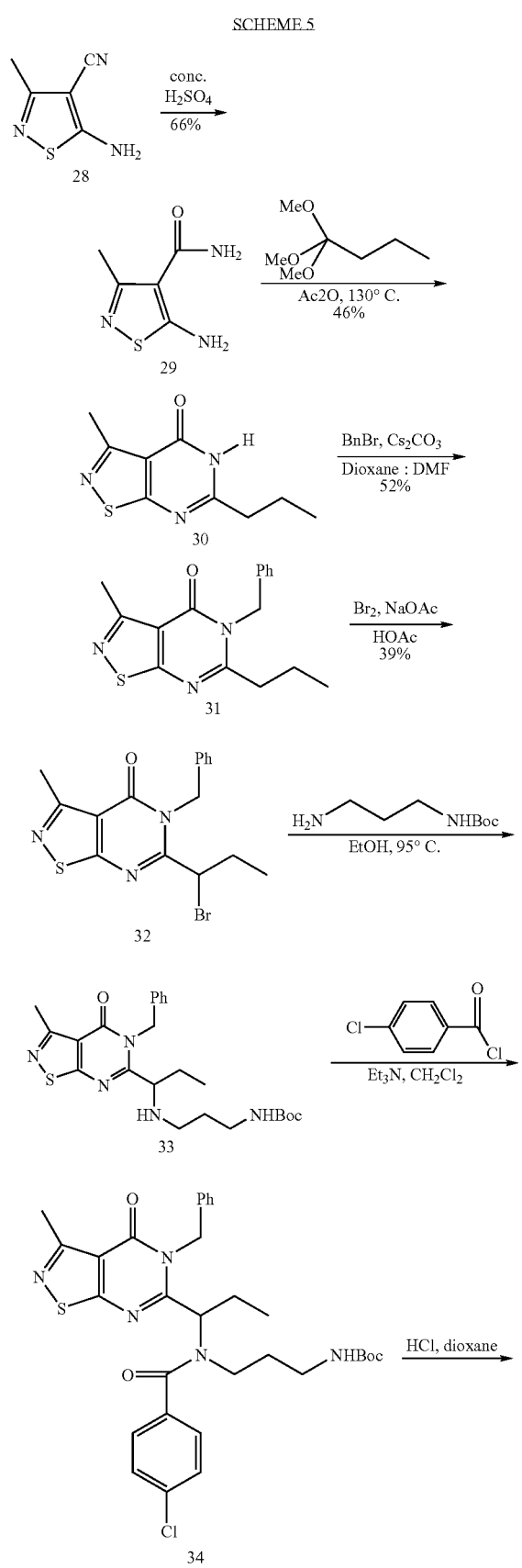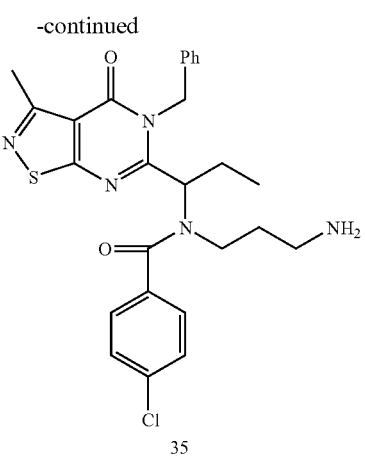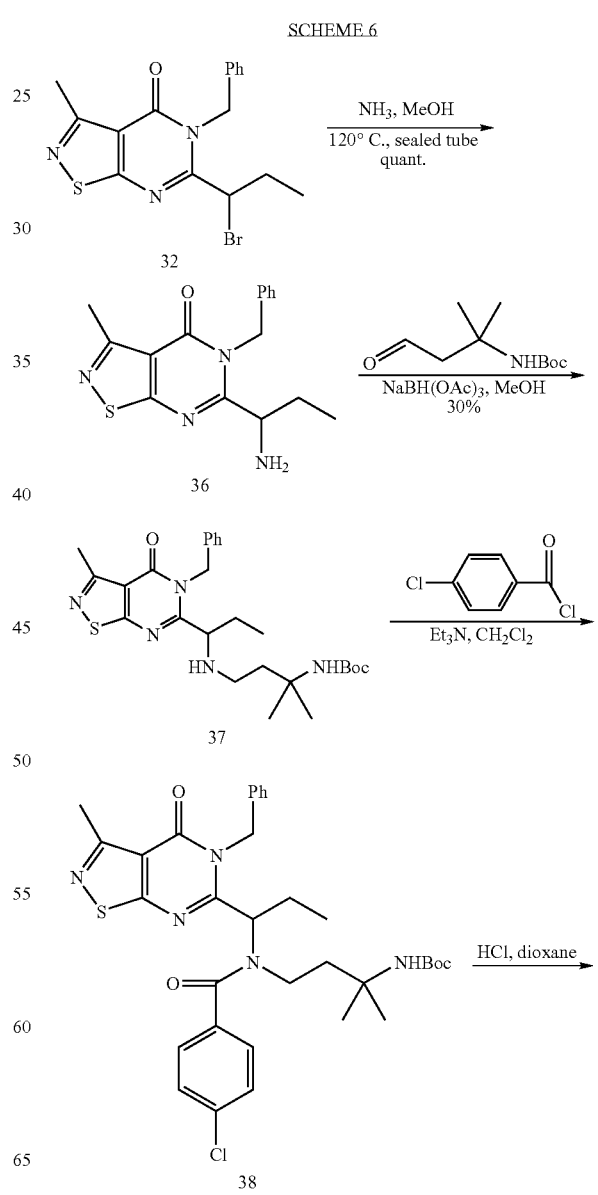

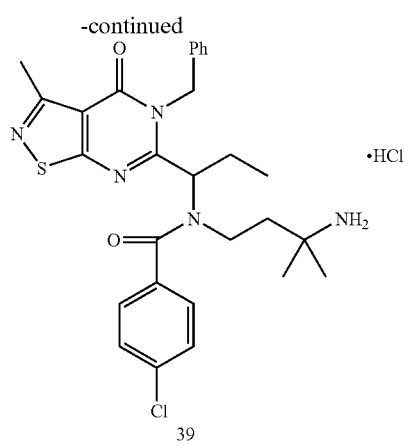

39

As previously discussed, Eg5 is a kinesin-like motor protein that facilitates spindle bipolarity during mitosis of the cell cycle. More specifically, the Eg5 protein acts to sort and bundle microtubules of the mitotic spindle during mitosis. Accordingly, Eg5 participates in cell cycle regulation through the spindle checkpoint during the M phase of the cycle. While not wishing to be bound by any theory, it is believed that the compounds of the instant invention act as Eg5 inhibitors. This is theorized because the compounds of the instant invention induce a monopolar astral array of microtubules (the monoastral phenotype) and it has been shown that when Eg5 activity is absent, the monoastral phenotype forms. Regardless of the mechanism of action, the compounds of the instant invention have been shown to cause disruption of the bipolar spindle, spindle checkpoint initiation, mitotic arrest, programmed cell death and tumor cell proliferation inhibition. Furthermore, the compounds of the invention induce a cell cycle arrest in mitosis that is not transient but rather which progresses into programmed cell death. The compounds also exhibit high potency, inducing mitotic arrest and apoptosis in human cells in vitro at concentrations in the low or sub μM range. Additionally, in contrast to microtubule agents, the compounds do not disrupt the dynamic instability of microtubules. The instant invention may therefore more specifically target the mitotic spindle of proliferating cells, which may provide for different toxicity profiles than those of existing anti-cancer drugs.

The compounds according to the invention have pharmacological properties; in particular, the compounds of the present invention induce mitotic arrest, cytoxiciy, and apoptosis and are believed to be Eg5 inhibitors. The novel compounds are thus useful in the therapy of a variety of proliferative diseases (including but not limited to diseases associated with the Eg5 motor protein) such as cancer, autoimmune diseases, viral diseases, fungal diseases, neurodegenerative disorders and cardiovascular disease.

More specifically, the compounds are useful in the treatment of a variety of cancers, including, but not limited to, the following:

a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

c) hematopoietic tumors of myeloid lineage, including acute and chronic myelogenous leukemias, myelodysplastic syndrome and promyelocytic leukemia;

d) tumors of mesenchymal origin, including fibrosarcoma and rhabdomyosarcoma;

e) tumors of the central and peripheral nervous system, including astrocytoma, neuroblastoma, glioma and schwannomas; and f) other tumors, including melanoma, seminoma, teratocarcinoma, osteosarcoma, xenoderoma pigmentosum, keratoctanthoma, thyroid follicular cancer and Kaposi's sarcoma.

Due to the key role of motor proteins in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of the present invention induce apoptosis. The apoptotic response is aberrant in a variety of human diseases. Compounds of the present invention, as modulators of apoptosis, will be useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of the present invention may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of the present invention may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of the present invention may also be useful in inhibiting tumor angiogenesis and metastasis.

The instant invention may also inhibit other motor proteins, for example, including but not limited to those human motor proteins that correspond to, Xklp2, MKLP1, CHO1, chromokinesins, Nod, Cenp-E, MCAK, members of the BimC family, and members of the Kar3 family. Additionally, compounds used in the methods of the instant invention may also act as inhibitors of other kinesin or kinesin-like proteins and thus be effective in the treatment of diseases associated with other kinesin or kinesin-like proteins.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones, either naturally occurring or synthetic; hormonal agents, such as tamoxifen; thymidilate synthase inhibitors, such as 5-fluorouracil; and anti-metabolites, such as methotrexate, tyrosine kinase inhibitors such as Iressa and OSI-774; angiogenesis inhibitors; EGF inhibitors; VEGF inhibitors; CDK inhibitors; Her1/2 inhibitors and monoclonal antibodies directed against growth factor receptors such as erbitux (EGF) and herceptin (Her2), SRC, C-Kit.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.TM. model 5400 intravenous pump.

The pharmaceutical compositions may be in the form of a sterile injectable aqueous or oleageneous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

ASSAYS

The pharmacological properties of the compounds of this invention may be confirmed by a number of pharmacological assays. The exemplified pharmacological assays that follow have been carried out with the compounds according to the invention and their salts. The compounds of the present invention exhibited antiproliferative activity.

Cell Culture

Cell lines are maintained in RPMI-1640 plus 10% fetal bovine serum.

72-Hour Proliferation Assay

Cells were plated at a density of 3,000–6,000 cells/well, depending upon the cell line used, in a 96-well plate. The cultures were grown overnight. Cells were then treated in triplicate with a seven concentration dose-response curve. The maximum concentration of DMSO never exceeded 0.5%. Cells were exposed to compound for 72 hours. Proliferation was measured using XTT or MTS from Promega. The ovarian, breast, prostate, lung, leukemia, and colorectal human cancer cell lines used in this assay included but were not limited to, for example, A2780S, SKBR3, MDA-MB-231, PC3, LX-1, K562, HT-29, WiDr, HCT-15 and HCT116. The compounds of the present invention exhibited activity in the 72-hour cell proliferation assay, inhibiting cell proliferation in one or more of the cell lines listed above with at an $IC_{50}$ less than or equal to about 10 µM.

Clonogenic Growth Assay

Colony growth inhibition was measured for A2780 ovarian carcinoma cells using a standard clonogenic assay. Briefly, 200 cells/well were seeded into 6-well tissue culture plates (Falcon, Franklin Lakes, N.J.) and allowed to attach for 18 hours. Assay medium consisted of RPMI-1640 plus 10% fetal bovine serum. Cells were then treated in duplicate with a six concentration dose-response curve. The maximum concentration of DMSO never exceeded 0.25%. Cells were exposed to compound for 4, 8 or 24 hours. Compound was then removed and the cells were washed with 2 volumes of PBS. The normal growth medium was then replaced. Colonies were fed with fresh media every third day. Colony number was scored on day 10–14 using a Optimax imaging station. The compound concentration required to inhibit 50% or 90% of colony formation ($IC_{50}$ or $IC_{90}$, respectively) was determined by non-linear regression analysis. The coefficient of variance (SD/mean, n=3)=30%. When exposed to cells for 24 hours, the compounds of the present invention exhibited activity in the clonogenecity assay.

Cell Cycle Analysis

The cell cycle profile of cells treated with compounds of the present invention was monitored by flow cytometry. Briefly, A2780 ovarian carcinoma cells were seeded at a density of $2 \times 10^5$ per well in standard 6 well culture plates and permitted to grow for 17 hours. Cells were then exposed to compounds of the present invention at varying concentrations for 2 to 24 hours. Following exposure, cell populations were harvested, stained with propidium iodide to determine DNA content and also stained with the appropriate immunological reagent for protein biomarkers of mitosis and apoptosis, including, for example, anti-phospho-ThreonineProline, anti-M Phase Phosphoprotein 2 (MMP2), and anti-p85 PARP. The compounds of the present invention exhibited activity in the cell cycle profile analysis assay, producing significant increases in mitotic and apoptotic fractions of the cell population.

Immunocytochemistry Assays

A2780 ovarian carcinoma cells or PTK2 kangaroo rat kidney epitheilal cells were plated at a density of 200 to 2000 cells per well in 4 chamber glass slides and allowed to attach overnight. Cells were then treated with compounds of the present invention at concentrations of 100 nM to 50 µM for 4 to 30 hours, fixed and permeabilized for subsequent staining. Stain reagents included, for example, propidium iodide, DAPI, rhodamine phalloidin, anti-αtubulin, anti-βtubulin, anti-γtubulin, and the appropriate fluorescent-tagged secondary antibodies. Cells were imaged by fluorescent and confocal fluorescent microscropy. The compounds of the present invention inhibited bipolar spindle formation and induced a monoastral array of microtubules.

Further subject matter of the invention also includes pharmaceuticals for use as described above including controlling cancer, inflammation and arthritis, which contain at least one compound of the present invention as defined above or at least one of its pharmacologically acceptable acid addition salts, and the use of a compound of the present invention for the preparation of a pharmaceutical having activity against proliferative diseases as described previously including against cancer, inflammation and/or arthritis.

The following examples and preparations describe the manner and process of making and using the invention and are illustrative rather than limiting. It should be understood that there may be other embodiments which fall within the spirit and scope of the invention as defined by the claims appended hereto.

EXAMPLES

All LC/MS data were obtained using the following conditions: (YMC S5 ODS 4.6×50 mm) column, 10–90% aqueous methanol containing 0.1% of TFA, gradient over 4 minutes at 4 mL/min flow rate, monitoring at 220 nm. The proton NMR spectra were obtained on a 400 or 500 MHz NMR instrument.

Example 1

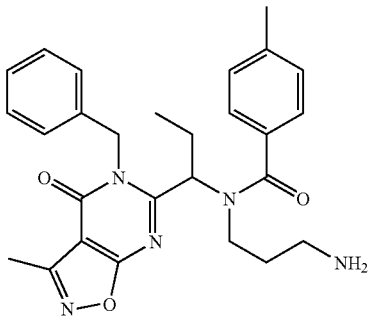

(±)-N-(3-Amino-propyl)-N-[1-(5-benzyl-3-methyl-4-oxo-4,5-dihydro-isoxazolo[5,4-d]pyrimidin-6-yl)-propyl]-4-methyl-benzamide Step 1: 5-Amino-3-methyl-isoxazole-4-carbonitrile.

A mixture of hydroxylamine hydrochloride (27.8 g, 0.4 mol) and sodium hydroxide (16.0 g, 0.4 mol) in water (1000 mL) was treated with 2-(1-ethoxy-ethylidene)-malononitrile (54.42 g, 0.4 mol) over 1 h. After the addition, the reaction mixture was stirred at room temperature for 18 h. The resulting suspension was collected, washed with cold EtOAc (1000 mL) and air dried to afford the desired product as a white solid (35.8 g, 72%); $^1$H NMR (DMSO-d$_6$) δ 8.32 (s, 2 H), 2.1 (s, 3H).

Step 2: 3-Methyl-6-propyl-5-H-isoxazolo[5,4-d]pyrimidin-4-one.

A 0° C. suspension of the compound of Example 1 Step 1 (2.5 g, 0.2 mol) in butyric anhydride (15 mL) was treated with concentrated H$_2$SO$_4$ (1.5 mL). The reaction mixture was warmed to 100° C. and stirred for 1 h. The mixture was cooled to room temperature and poured into ice water. The resulting white precipitate was collected, washed with water and air dried to give the desired product as a white solid (2.0 g, 52%); $^1$H NMR (DMSO-d$_6$) δ 2.61 (t, J=7.5 Hz, 2H), 2.42 (s, 3H), 1.70 (q, J=7.5 Hz, 2H), 0.89 (t, J=7.5 Hz, 3H); LC/MS (ESI): 194 (M+H)$^+$.

Step 3: 5-Benzyl-3-methyl-6-propyl-5H-isoxazolo[5,4-d]pyrimidin-4-one.

A suspension of the compound of Example 1 Step 2 (1.8 g, 9.3 mmol) in anhydrous THF (40 mL) at room temperature was treated with 1M lithium hexamethyldisilazide (13.9 mL, 13.9 mmol) and stirred for 1 h. The mixture was then treated with benzylbromide (2.37 g, 1.65 mL, 13.9 mmol) and NaI (0.15 g, 1.0 mmol). The mixture was stirred at 50° C. for 40 h, then cooled to room temperature. The mixture was partitioned between ether and brine and the organic phase was washed with water. The organic phase was concentrated under vacuum and purified by flash chromatography on SiO$_2$ (15% EtOAc/Hexane) to afford the desired product as a white solid (540 mg, 20%); $^1$H NMR (DMSO-d$_6$) δ 7.35 (m, 5H), 5.41 (s, 2H), 2.79 (t, J=7.5 Hz, 2H), 2.53 (s, 3H), 1.72 (q, J=7.5 Hz, 2H), 0.90 (t, J=7.5 Hz, 3H); LC/MS (ESI): 284 (M+H)$^+$.

Step 4: (±)-5-Benzyl-6-(1-bromo-propyl)-3-methyl-5H-isoxazolo[5,4-d]pyrimidin-4-one.

A solution of the compound of Example 1, Step 3 (525 mg, 1.85 mmol) in HOAc (20 mL) at room temperature was treated with NaOAc (182 mg, 2.22 mmol) followed by Br$_2$ (296 mg, 1.85 mmol). The mixture was stirred at 55° C. for 72 h then cooled and poured into water. The resulting precipitate was collected and air dried to afford the desired product as a white solid (200 mg, 30%); $^1$H NMR (DMSO-d$_6$) δ 7.35 (m, 5H), 5.71 (d, J=16.5 Hz, 1H), 5.21 (d, J=16.5 Hz, 1H), 5.16 (t, J=7.5 Hz, 1H), 2.51 (s, 3H), 2.49 (m, 1H), 2.28 (m, 1H), 0.78 (t, J=7.5 Hz, 3H); LC/MS (ESI): 284 (M+H)$^+$.

Step 5: (±)-{3-[1-(5-Benzyl-3-methyl-4-Oxo-4,5-dihydro-isoxazolo[5,4-d]pyrimidin-6-yl)-propylamino]-propyl}-carbamic acid tert-butyl ester.

A solution the compound of Example 1 Step 4 (200 mg, 0.55 mmol) in EtOH (25 mL) was treated with N-BOC-1, 3-diaminopropane (240 mg, 1.38 mmol) and stirred at reflux for 6 h. The mixture was cooled to room temperature and concentrated under vacuum. The residue was purified by flash chromatography on SiO$_2$ (50% EtOAc/Hexane) to afford the desired product as a yellow oil (165 mg, 66%); $^1$H NMR (DMSO-d$_6$) δ 7.35 (m, 5H), 5.47 (m, 2H), 4.67 (s, 1H), 2.84 (m, 2H), 2.54 (m, 2H), 2.50 (s, 3H), 1.83 (m, 2H), 1.60 (m, 2H), 1.37 (s, 9H), 0.71 (m, 3H); (LC/MS (ESI): 456 (M+H)$^+$.

Step 6: (±)-{3-[[1-(5-Benzyl-3-methyl-4-oxo-4,5-dihydro-isoxazolo[5,4-d]pyrimidin-6-yl)-propyl]-(4-methyl-benzoyl)-amino]-propyl}-carbamic acid tert-butyl ester.

A solution of the compound of Example 1 Step 5 (50 mg, 0.11 mmol) in CHCl$_3$ (10 mL) was treated with 4-toluoyl chloride (16.9 mg, 0.11 mmol) followed by Et$_3$N (11.1 mg, 0.11 mmol). The resulting mixture was stirred at room temperature for 18 h, then concentrated under vacuum. The crude product was purified by preparative reverse-phase HPLC on a YMC S5 ODS 30×100 mm column to afford the desired product as a yellow glass (60 mg, 95%); LC/MS 100% at 4.32 min (ESI): 574 (M+H)$^+$.

Step 7: (±)-N-(3-Amino-propyl)-N-[1-(5-benzyl-3-methyl-4-oxo-4,5-dihydro-isoxazolo[5,4-d]pyrimidin-6-yl)-propyl]-4-methyl-benzamide.

A solution of the compound from Example 1 Step 6 (60 mg, 0.10 mmol) in CH$_2$Cl$_2$ (2.5 mL) at room temperature was treated with Et₃SiH (150 mL) followed by TFA (1.0 mL). The reaction mixture was stirred for 0.5 h then concentrated under vacuum to the desired product as a colorless film (32 mg, 65%); ¹H NMR (DMSO-d₆) δ 7.62 (s, 1H), 7.25 (m, 7H), 7.22 (s, 1H), 5.77 (d, J=16.5 Hz, 1H), 5.39 (s, 1H), 4.90 (d, J=15.9 Hz, 1H), 3.40 (t, J=7.0 Hz, 2H), 2.92 (s, 3H), 2.54 (s, 3H), 2.09 (m, 1H), 1.92 (m, 1H), 1.91 (m, 1H), 1.89 (t, J=7.0 Hz, 3H), 0.68 (m, 1H); LC/MS (ESI): 474 (M+H)⁺.

Example 2

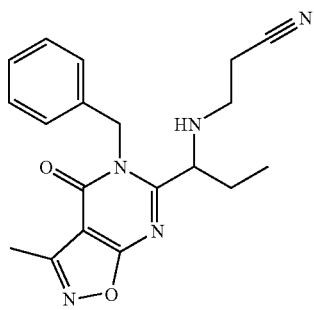

(±)-3-[1-(5-Benzyl-3-methyl-4-oxo-4,5-dihydro-isoxazolo[5,4-d]pyrimidin-6-yl)-propylamino]-propionitrile A solution of the compound of Example 1 Step 4 (2.0 g, 5.5 mmol) in EtOH (50 mL) treated 3-amino-propionitrile (1.55 g, 22.1 mmol) and stirred at reflux for 6 h. The mixture was cooled to room temperature and concentrated under vacuum. The resulting material was purified by preparative reverse-phase HPLC (CH₃OH/H₂O) on a YMC S10 ODS 50×500 mm column to afford the desired product as a yellow glass (1.2 g, 62%); ¹H NMR (CD₃OD): δ 7.38 (m, 5H), 5.65 (d, J=16.5 Hz, 1H), 5.30 (d, J=16.5 Hz, 1H), 4.65 (t, J=6.0 Hz, 1H), δ 3.15 (m, 1H), 2.72 (m, 1H), 2.70 (t, J=7.5 Hz, 2H), 2.59 (s, 3H), 1.92 (m, 2H), 0.89 (t, J=7.5 Hz, 3H)); LC/MS (ESI): 352 (M+H)⁺.

Examples 3 through 9 were prepared from the product of Example 1 Step 4 according to the methods of Example 1 Steps 5 & 6 with the appropriate amine and toluoyl chloride respectively.

Example 3

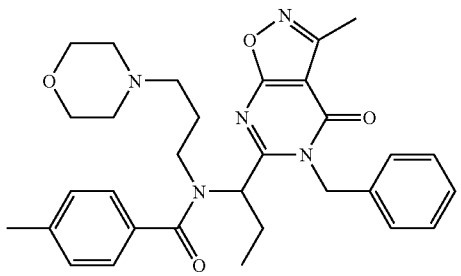

(±)-N-[1-(5-Benzyl-3-methyl-4-oxo-4,5-dihydro-isoxazolo[5,4-d]pyrimidin-6-yl)-propyl]-4-methyl-N-(3-morpholin-4-yl-propyl)-benzamide Yield: 10%; LC/MS 91% at 3.02 min (ESI): 544 (M+H)⁺.

Example 4

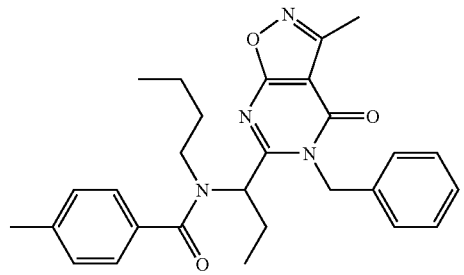

(±)-N-[1-(5-Benzyl-3-methyl-4-oxo-4,5-dihydro-isoxazolo[5,4-d]pyrimidin-6-yl)-propyl]-N-butyl-4-methyl-benzamide Yield: 29%; LC/MS at 3.02 min (ESI): 473 (M+H)⁺.

Example 5

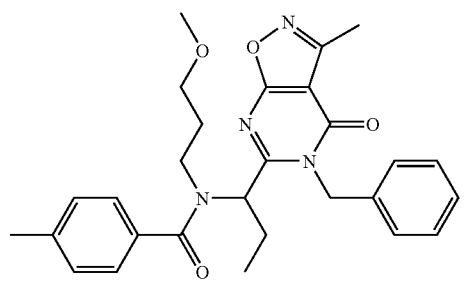

(±)-N-[1-(5-Benzyl-3-methyl-4-oxo-4,5-dihydro-isoxazolo[5,4-d]pyrimidin-6-yl)-propyl]-N-(3-methoxy-propyl)-4-methyl-benzamide Yield: 75%; LC/MS 95% at 3.69 min (ESI): 489 (M+H)⁺.

Example 6

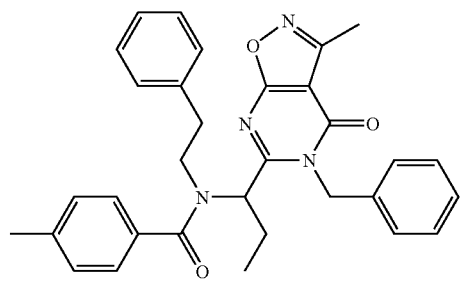

(±)-N-[1-(5-Benzyl-3-methyl-4-oxo-4,5-dihydro-isoxazolo[5,4-d]pyrimidin-6-yl)-propyl]-4-methyl-N-phenethyl-benzamide Yield: 38%; LC/MS 98% at 4.01 min (ESI): 521 (M+H)⁺.

Example 7

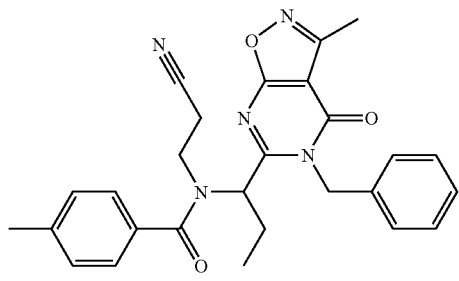

(±)-N-[1-(5-Benzyl-3-methyl-4-oxo-4,5-dihydro-isoxazolo[5,4-d]pyrimidin-6-yl)-propyl]-N-(2-cyano-ethyl)-4-methyl-benzamide Yield: 8%; LC/MS 95% at 3.31 min (ESI): 470 (M+H)$^+$.

Example 8

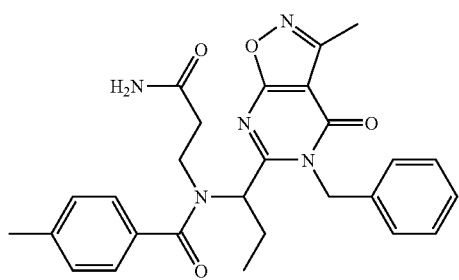

(±)-N-[1-(5-Benzyl-3-methyl-4-oxo-4,5-dihydro-isoxazolo[5,4-d]pyrimidin-6-yl)-propyl]-N-(2-carbamoyl-ethyl)-4-methyl-benzamide Yield: 9%; LC/MS 95% at 3.18 min (ESI): 488 (M+H)$^+$.

Example 9

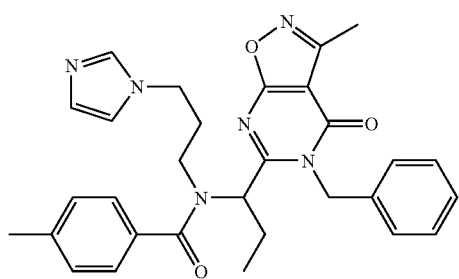

(±)-N-[1-(5-Benzyl-3-methyl-4-oxo-4,5-dihydro-isoxazolo[5,4-d]pyrimidin-6-yl)-propyl]-N-(3-imidazol-1-yl-propyl)-4-methyl-benzamide Yield: 40%; LC/MS 98% at 2.79 min (ESI): 525 (M+H)$^+$.

Compounds in the Examples 10 through 37 were prepared in parallel according to the method of Example 1 Step 6 with the product of Example 2 and the appropriate acid chloride.

Example 10

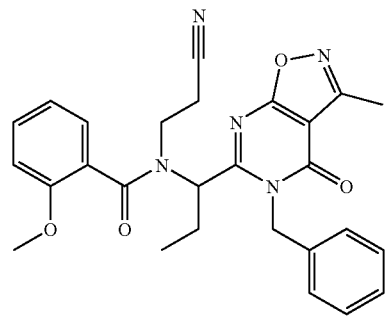

(±)-N-[1-(5-Benzyl-3-methyl-4-oxo-4,5-dihydro-isoxazolo[5,4-d]pyrimidin-6-yl)-propyl]-N-(2-cyano-ethyl)-2-methoxy-benzamide Yield: 29%; LC/MS 100% at 3.20 min (ESI): 486 (M+H)$^+$.

Example 11

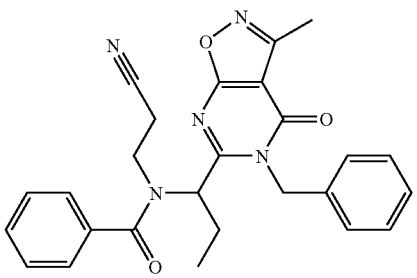

(±)-N-[1-(5-Benzyl-3-methyl-4-oxo-4,5-dihydro-isoxazolo[5,4-d]pyrimidin-6-yl)-propyl]-N-(2-cyano-ethyl)-benzamide Yield: 6.2%; LC/MS 76% at 3.23 min (ESI): 456 (M+H)$^+$.

Example 12

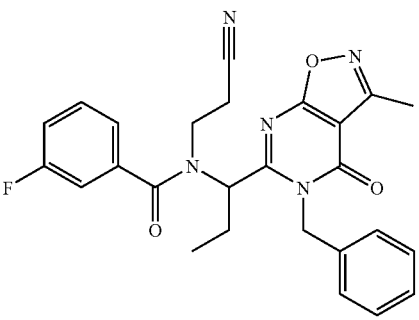

(±)-N-[1-(5-Benzyl-3-methyl-4-oxo-4,5-dihydro-isoxazolo[5,4-d]pyrimidin-6-yl)-propyl]-N-(2-cyano-ethyl)-3-fluoro-benzamide Yield: 10%; LC/MS 100% at 3.25 min (ESI): 486 (M+H)$^+$.

Example 13

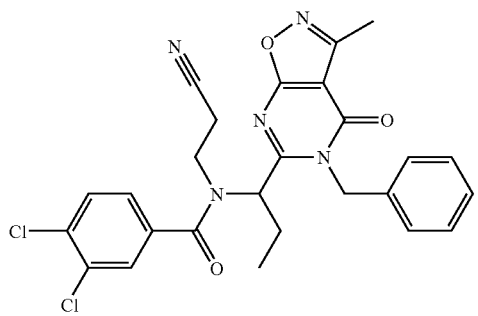

(±)-N-[1-(5-Benzyl-3-methyl-4-oxo-4,5-dihydro-
isoxazolo[5,4-d]pyrimidin-6-yl)-propyl]-3,4-
dichloro-N-(2-cyano-ethyl)-benzamide Yield: 10%; LC/MS 98% at 3.64 min (ESI): 524 (M+H)+.

Example 14

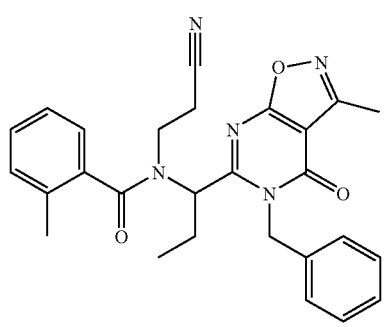

(±)-N-[1-(5-Benzyl-3-methyl-4-oxo-4,5-dihydro-
isoxazolo[5,4-d]pyrimidin-6-yl)-propyl]-N-(2-cy-
ano-ethyl)-2-methyl-benzamide Yield: 1.5%; LC/MS 82% at 3.32 min (ESI): 470 (M+H)+.

Example 15

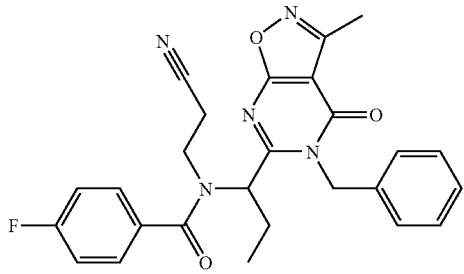

(±)-N-[1-(5-Benzyl-3-methyl-4-oxo-4,5-dihydro-
isoxazolo[5,4-d]pyrimidin-6-yl)-propyl]-N-(2-cy-
ano-ethyl)-4-fluoro-benzamide Yield: 6.8%; LC/MS 85% at 3.25 min (ESI): 474 (M+H)+.

Example 16

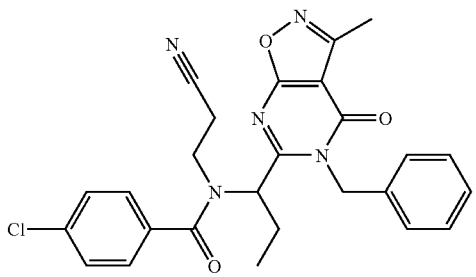

(±)-N-[1-(5-Benzyl-3-methyl-4-oxo-4,5-dihydro-
isoxazolo[5,4-d]pyrimidin-6-yl)-propyl]-4-chloro-N-
(2-cyano-ethyl)-benzamide Yield: 6.6%; LC/MS 88% at 3.41 min (EST): 490 (M+H)+.

Example 17

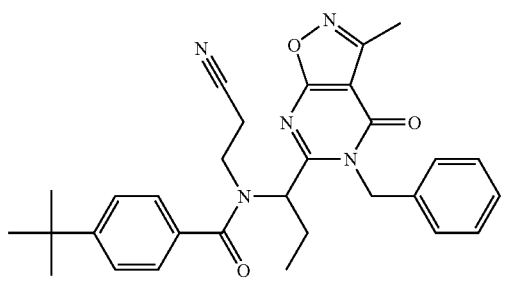

(±)-N-[1-(5-Benzyl-3-methyl-4-oxo-4,5-dihydro-
isoxazolo[5,4-d]pyrimidin-6-yl)-propyl]-4-tert-butyl-
N-(2-cyano-ethyl)-benzamide Yield: 15.1%; LC/MS 79% at 3.81 min (ESI): 512 (M+H)+.

Example 18

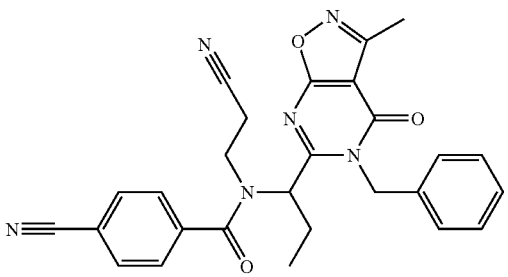

(±)-N-[1-(5-Benzyl-3-methyl-4-oxo-4,5-dihydro-
isoxazolo[5,4-d]pyrimidin-6-yl)-propyl]-4-cyano-N-
(2-cyano-ethyl)-benzamide Yield: 19.3%; LC/MS 97% at 3.09 inin (ESI): 481 (M+H)+.

Example 19

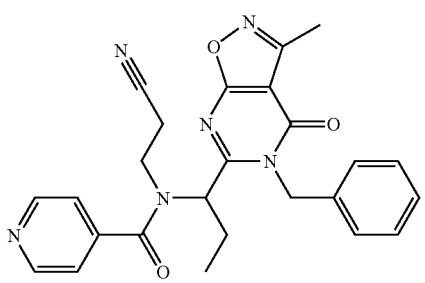

(±)-N-[1-(5-Benzyl-3-methyl-4-oxo-4,5-dihydro-isoxazolo[5,4-d]pyrimidin-6-yl)-propyl]-N-(2-cyano-ethyl)-isonicotinamide Yield: 42.1%; LC/MS 100% at 2.78 min (ESI): 457 (M+H)$^+$.

Example 20

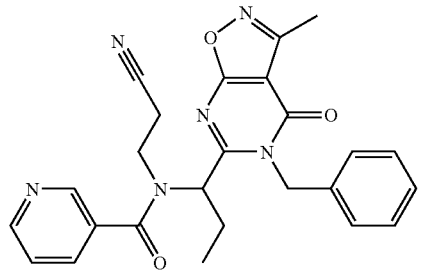

(±)-N-[1-(5-Benzyl-3-methyl-4-oxo-4,5-dihydro-isoxazolo[5,4-d]pyrimidin-6-yl)-propyl]-N-(2-cyano-ethyl)-nicotinamide Yield: 16%; LC/MS 92% at 2.84 min (ESI): 457 (M+H)$^+$.

Example 21

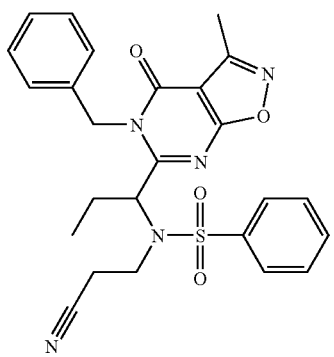

(±)-N-[1-(5-Benzyl-3-methyl-4-oxo-4,5-dihydro-isoxazolo[5,4-d]pyrimidin-6-yl)-propyl]-N-(2-cyano-ethyl)-benzenesulfonamide Yield: 23.8%; LC/MS 92% at 3.39 min (ESI): 492 (M+H)$^+$.

Example 22

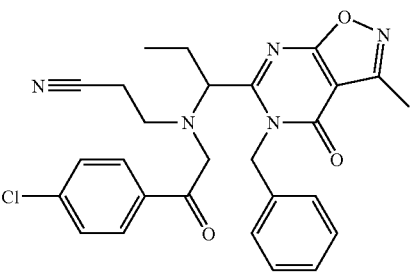

(±)-3-{[1-(5-Benzyl-3-methyl-4-oxo-4,5-dihydro-isoxazolo[5,4-d]pyrimidin-6-yl)-propyl]-[2-(4-chloro-phenyl)-2-oxo-ethyl]-amino}-propionitrile Yield: 24.9%; LC/MS 100% at 3.60 min (ESI): 504 (M+H)$^+$.

Example 23

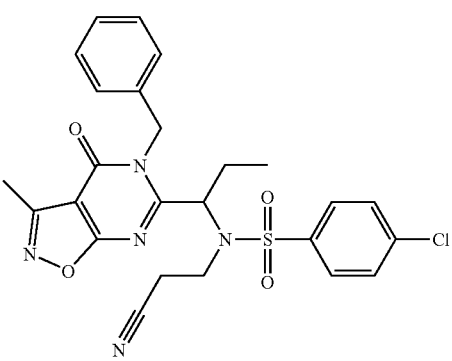

(±)-N-[1-(5-Benzyl-3-methyl-4-oxo-4,5-dihydro-isoxazolo[5,4-d]pyrimidin-6-yl)-propyl]-4-chloro-N-(2-cyano-ethyl)-benzenesulfonamide Yield: 1.3%; LC/MS 100% at 3.63 min (ESI): 526 (M+H)$^+$.

Example 24

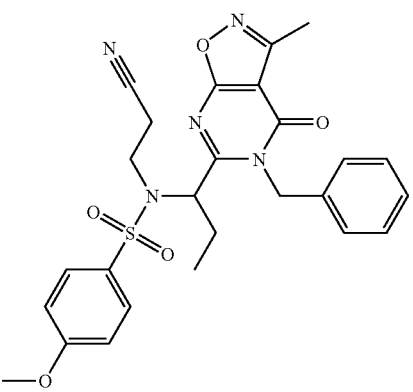

(±)-N-[1-(5-Benzyl-3-methyl-4-oxo-4,5-dihydro-isoxazolo[5,4-d]pyrimidin-6-yl)-propyl]-N-(2-cyano-ethyl)-4-methoxy-benzenesulfonamide Yield: 4.1%; LC/MS 96% at 3.29 min (ESI): 522 (M+H)$^+$.

Example 25

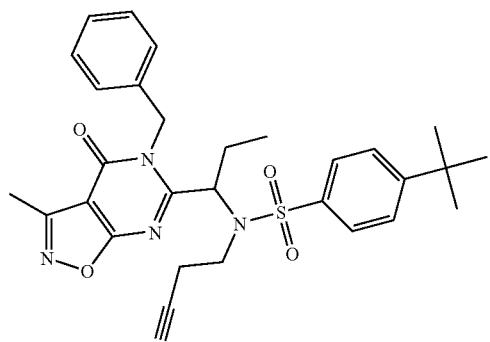

(±)-N-[1-(5-Benzyl-3-methyl-4-oxo-4,5-dihydro-isoxazolo[5,4-d]pyrimidin-6-yl)-propyl]-4-tert-butyl-N-(2-cyano-ethyl)-benzenesulfonamide Yield: 1.0%; LC/MS 100% at 3.90 min (ESI): 548.6 (M+H)+.

Example 26

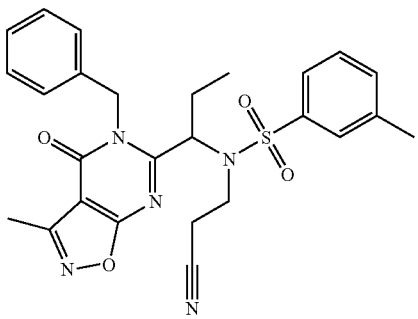

(±)-N-[1-(5-Benzyl-3-methyl-4-oxo-4,5-dihydro-isoxazolo[5,4-d]pyrimidin-6-yl)-propyl]-N-(2-cyano-ethyl)-3-methyl-benzenesulfonamide Yield: 2.8%; LC/MS 70% at 3.57 min (ESI): 506 (M+H)+.

Example 27

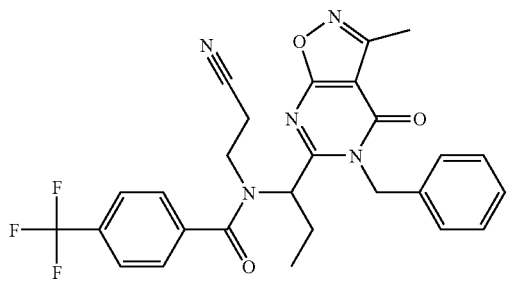

(±)-N-[1-(5-Benzyl-3-methyl-4-oxo-4,5-dihydro-isoxazolo[5,4-d]pyrimidin-6-yl)-propyl]-N-(2-cyano-ethyl)-4-trifluoromethyl-benzamide Yield: 16.7%; LC/MS 100% at 3.49 min (ESI): 524 (M+H)+.

Example 28

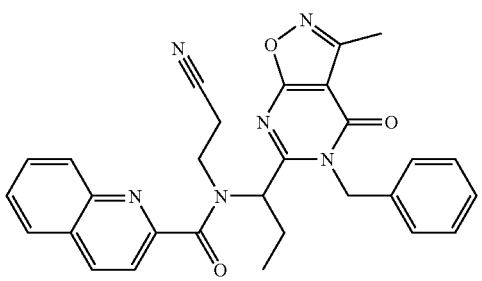

(±)-Quinoline-2-carboxylic acid [1-(5-benzyl-3-methyl-4-oxo-4,5-dihydro-isoxazolo[5,4-d]pyrimidin-6-yl)-propyl]-(2-cyano-ethyl)-amide Yield: 48.9%; LC/MS 95% at 3.58 min (ESI): 507 (M+H)+.

Example 29

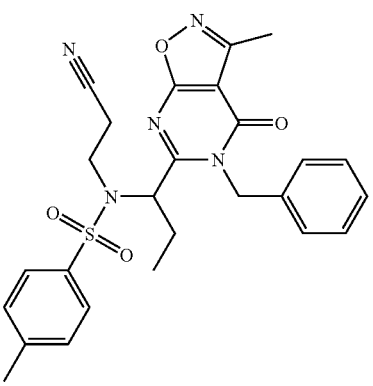

(±)-N-[1-(5-Benzyl-3-methyl-4-oxo-4,5-dihydro-isoxazolo[5,4-d]pyrimidin-6-yl)-propyl]-N-(2-cyano-ethyl)-4-methyl-benzenesulfonamide Yield: 1.90%; LC/MS 100% at 3.58 min (ESI): 506 (M+H)+.

Example 30

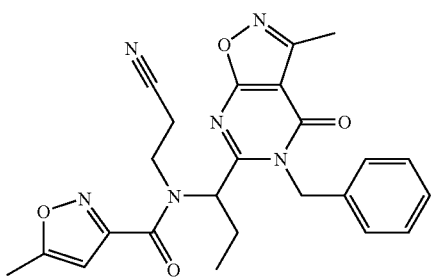

(±)-5-Methyl-isoxazole-3-carboxylic acid [1-(5-benzyl-3-methyl-4-oxo-4,5-dihydro-isoxazolo[5,4-d]pyrimidin-6-yl)-propyl]-(2-cyano-ethyl)-amide Yield: 49.5%; LC/MS 100% at 3.52 min (ESI): 461 (M+H)+.

Example 31

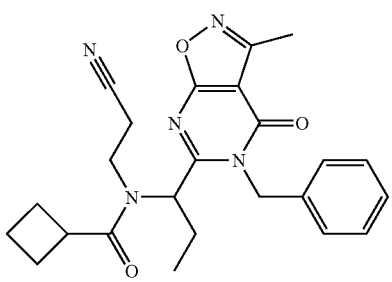

(±)-Cyclobutanecarboxylic acid [1-(5-benzyl-3-methyl-4-oxo-4,5-dihydro-isoxazolo[5,4-d]pyrimidin-6-yl)-propyl]-(2-cyano-ethyl)-amide Yield: 6.8%; LC/MS 90% at 3.29 min (ESI): 434 (M+H)⁺.

Example 32

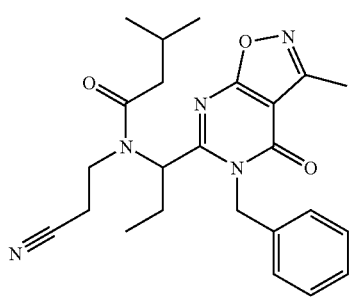

(±)-N-[1-(5-Benzyl-3-methyl-4-oxo-4,5-dihydro-isoxazolo[5,4-d]pyrimidin-6-yl)-propyl]-N-(2-cyano-ethyl)-3-methyl-butyramide Yield: 1.6%; LC/MS 75% at 3.38 min (ESI): 436 (M+H)⁺.

Example 33

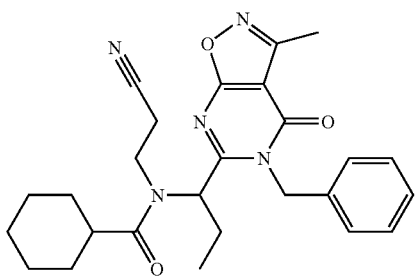

(±)-Cyclohexanecarboxylic acid [1-(5-benzyl-3-methyl-4-oxo-4,5-dihydro-isoxazolo[5,4-d]pyrimidin-6-yl)-propyl]-(2-cyano-ethyl)-amide Yield: 8.2%; LC/MS 92% at 3.54 min (ESI): 462 (M+H)⁺.

Example 34

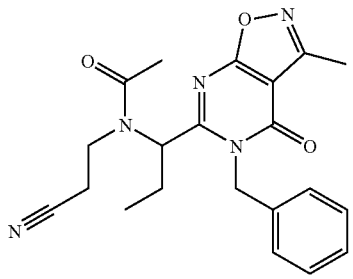

(±)-N-[1-(5-Benzyl-3-methyl-4-oxo-4,5-dihydro-isoxazolo[5,4-d]pyrimidin-6-yl)-propyl]-(2-cyano-ethyl)-acetamide Yield: 4.7%; LC/MS 100% at 2.94 min (ESI): 394 (M+H)⁺.

Example 35

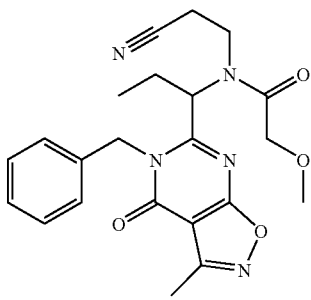

(±)-N-[1-(5-Benzyl-3-methyl-4-oxo-4,5-dihydro-isoxazolo[5,4-d]pyrimidin-6-yl)-propyl]-(2-cyano-ethyl)-2-methoxy-acetamide Yield: 44.2%; LC/MS 100% at 2.91 min (ESI): 424 (M+H)⁺.

Example 36

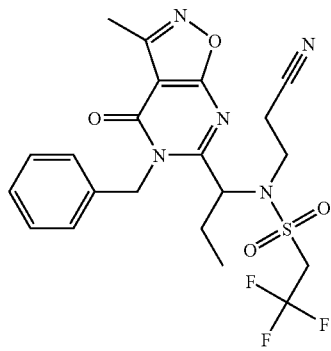

(±)-2,2,2-Trifluoro-ethanesulfonic acid [1-(5-benzyl-3-methyl-4-oxo-4,5-dihydro-isoxazolo[5,4-d]pyrimidin-6-yl)-propyl]-(2-cyano-ethyl)-amide Yield: 14.4%; LC/MS 77% at 3.25 min (ESI): 498 (M+H)⁺.

Example 37

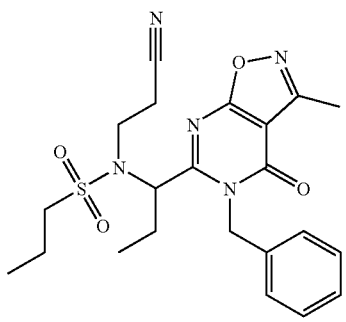

(±)-Propane-1-sulfonic acid [1-(5-benzyl-3-methyl-4-oxo-4,5-dihydro-isoxazolo[5,4-d]pyrimidin-6-yl)-propyl]-(2-cyano-ethyl)-amide Yield: 1.0%; LC/MS 100% at 3.64 min (ESI): 458 (M+H)$^+$.

Example 38

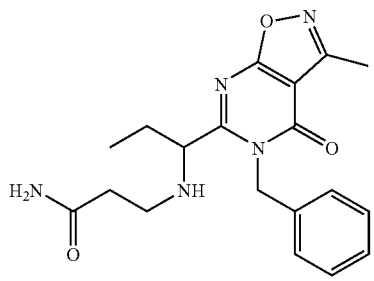

(±)-3-[1-(5-Benzyl-3-methyl-4-oxo-4,5-dihydro-isoxazolo[5,4-d]pyrimidin-6-yl)-propylamino]-propionamide A solution of the compound of Example 1 Step 4 (2.0 g, 5.5 mmol) in EtOH (50 mL) was treated with 3-aminopropionamide hydrochloride (1.72 g, 13.8 mmol) and DIEA (0.53 g, 27.7 mmol). The resulting mixture was stirred at reflux for 6 h, then cooled to room temperature and concentrated under vacuum. The crude product was dissolved in CH$_3$OH and purified by preparative reverse-phase HPLC (CH$_3$OH/H$_2$O) on a YMC S10 ODS 50×500 mm column to afford the desired product as a yellow glass (0.96 g, 49%); $^1$H NMR (CD$_3$OD): δ 7.37 (m, 5H), 5.65 (d, J=16.5 Hz, 1H), 5.30 (d, J=16.5 Hz, 1H), 4.70 (t, J=6.0 Hz, 1H), 3.15 (m, 1H), 2.94 (m, 1H), 2.59 (s, 3H), 2.49 (m, 2H), 1.93 (m, 2H), 0.89 (t, J=7.5 Hz, 3H); LC/MS (ESI): 370 (M+H)$^+$.

Examples 39 through 64 were prepared in parallel according to the method of Example 1 Step 6 with the product of Example 38 and an appropriate acid chloride.

Example 39

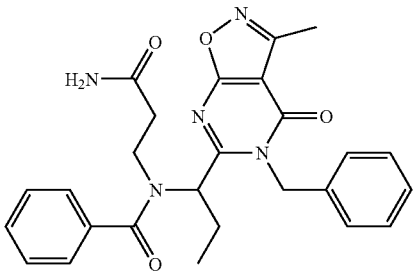

(±)-N-[1-(5-Benzyl-3-methyl-4-oxo-4,5-dihydro-isoxazolo[5,4-d]pyrimidin-6-yl)-propyl]-N-(2-carbamoyl-ethyl)-benzamide Yield: 39.4%; LC/MS 98% at 2.78 min (ESI): 474.5 (M+H)$^+$.

Example 40

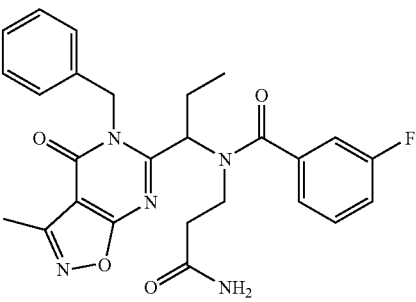

(±)-N-[1-(5-Benzyl-3-methyl-4-oxo-4,5-dihydro-isoxazolo[5,4-d]pyrimidin-6-yl)-propyl]-N-(2-carbamoyl-ethyl)-3-fluoro-benzamide Yield: 21.4%; LC/MS 96% at 2.76 min (ESI): 492.5 (M+H)$^+$.

Example 41

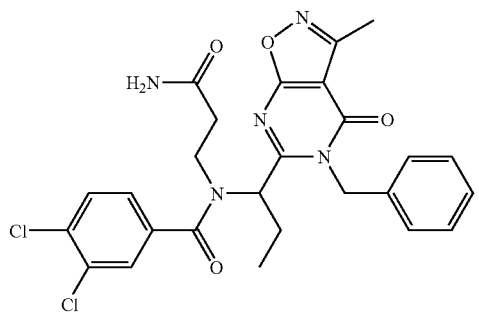

(±)-N-[1-(5-Benzyl-3-methyl-4-oxo-4,5-dihydro-isoxazolo[5,4-d]pyrimidin-6-yl)-propyl]-N-(2-carbamoyl-ethyl)-3,4-dichloro-benzamide Yield: 16.4%; LC/MS 92% at 3.19 min (ESI): 542.4 (M+H)$^+$.

Example 42

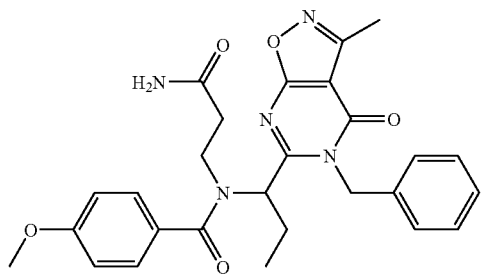

(±)-N-[1-(5-Benzyl-3-methyl-4-oxo-4,5-dihydro-isoxazolo[5,4-d]pyrimidin-6-yl)-propyl]-N-(2-carbamoyl-ethyl)-4-methoxy-benzamide Yield: 14.4%; LC/MS 90% at 2.83 min (ESI): 504.5 (M+H)$^+$.

Example 43

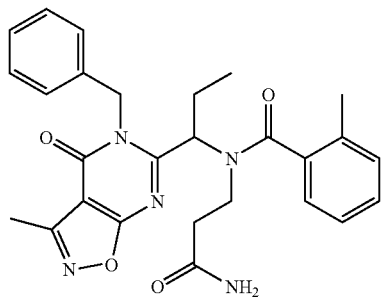

(±)-N-[1-(5-Benzyl-3-methyl-4-oxo-4,5-dihydro-isoxazolo[5,4-d]pyrimidin-6-yl)-propyl]-N-(2-carbamoyl-ethyl)-2-methyl-benzamide Yield: 12.3%; LC/MS 80% at 2.90 min (ESI): 488.5 (M+H)$^+$.

Example 44

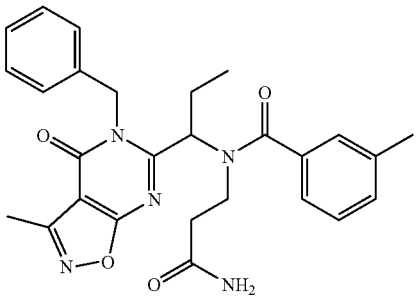

(±)-N-[1-(5-Benzyl-3-methyl-4-oxo-4,5-dihydro-isoxazolo[5,4-d]pyrimidin-6-yl)-propyl]-N-(2-carbamoyl-ethyl)-3-methyl-benzamide Yield: 22.2%; LC/MS 94% at 2.94 min (ESI): 488.5 (M+H)$^+$.

Example 45

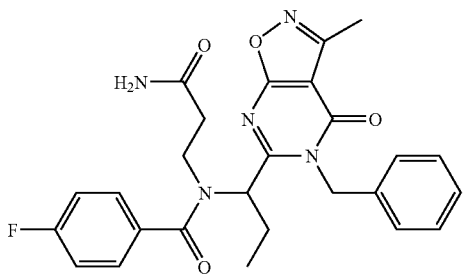

(±)-N-[1-(5-Benzyl-3-methyl-4-oxo-4,5-dihydro-isoxazolo[5,4-d]pyrimidin-6-yl)-propyl]-N-(2-carbamoyl-ethyl)-4-fluoro-benzamide Yield: 26.3%; LC/MS 90% at 2.82 min (ESI): 492.4 (M+H)$^+$.

Example 46

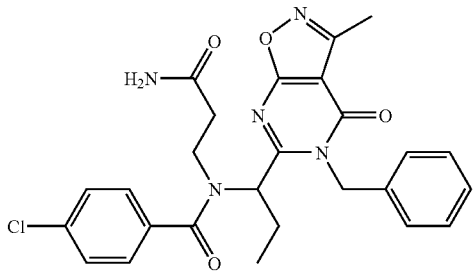

(±)-N-[1-(5-Benzyl-3-methyl-4-oxo-4,5-dihydro-isoxazolo[5,4-d]pyrimidin-6-yl)-propyl]-N-(2-carbamoyl-ethyl)-4-chloro-benzamide Yield: 26.2%; LC/MS 94% at 3.00 min (ESI): 508.5 (M+H)$^+$.

Example 47

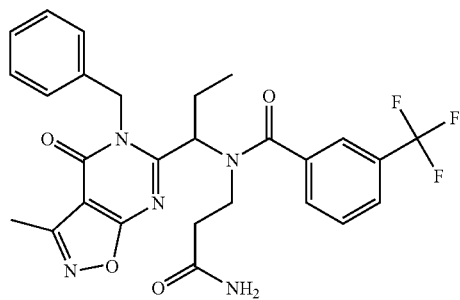

(±)-N-[1-(5-Benzyl-3-methyl-4-oxo-4,5-dihydro-isoxazolo[5,4-d]pyrimidin-6-yl)-propyl]-N-(2-carbamoyl-ethyl)-3-trifluoromethyl-benzamide Yield: 19.5%; LC/MS 80% at 2.90 min (ESI): 542.5 (M+H)$^+$.

Example 48

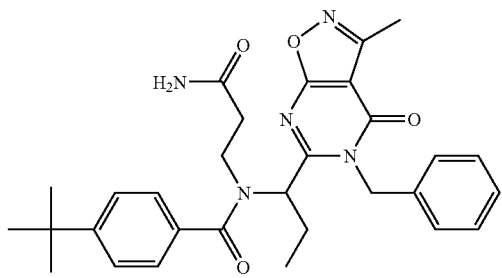

(±)-N-[1-(5-Benzyl-3-methyl-4-oxo-4,5-dihydro-isoxazolo[5,4-d]pyrimidin-6-yl)-propyl]-4-tert-butyl-N-(2-carbamoyl-ethyl)-benzamide Yield: 32.2%; LC/MS 76% at 2.78 min (ESI): 530 (M+H)$^+$.

Example 49

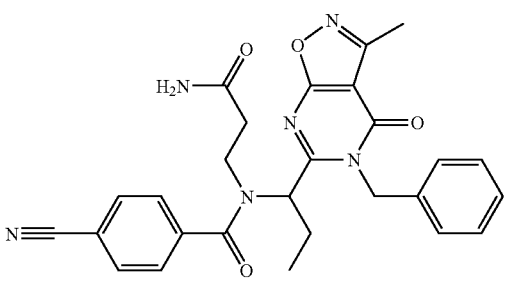

(±)-N-[1-(5-Benzyl-3-methyl-4-oxo-4,5-dihydro-isoxazolo[5,4-d]pyrimidin-6-yl)-propyl]-N-(2-carbamoyl-ethyl)-4-cyano-benzamide Yield: 7.0%; LC/MS 94% at 2.67 min (ESI): 499.5 (M+H)$^+$.

Example 50

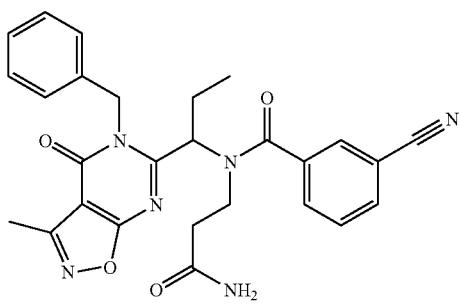

(±)-N-[1-(5-Benzyl-3-methyl-4-oxo-4,5-dihydro-isoxazolo[5,4-d]pyrimidin-6-yl)-propyl]-N-(2-carbamoyl-ethyl)-3-cyano-benzamide Yield: 22.1%; LC/MS 88% at 2.65 min (ESI): 499.5 (M+H)$^+$.

Example 51

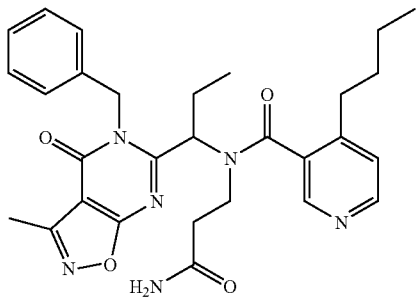

(±)-N-[1-(5-Benzyl-3-methyl-4-oxo-4,5-dihydro-isoxazolo[5,4-d]pyrimidin-6-yl)-propyl]-butyl-N-(2-carbamoyl-ethyl)-nicotinamide Yield: 7.9%; LC/MS 98% at 2.40 min (ESI): 475.5 (M+H)$^+$.

Example 52

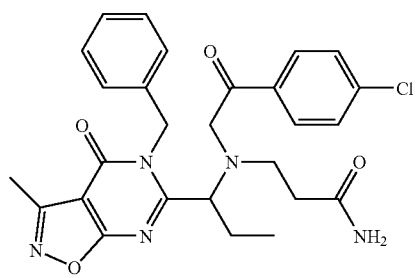

(±)-3-{[1-(5-Benzyl-3-methyl-4-oxo-4,5-dihydro-isoxazolo[5,4-d]pyrimidin-6-yl)-propyl]-[2-(4-chloro-phenyl)-2-oxo-ethyl]-amino}-propionamide Yield: 11.9%; LC/MS 97% at 3.22 min (ESI): 522.5 (M+H)$^+$.

Example 53

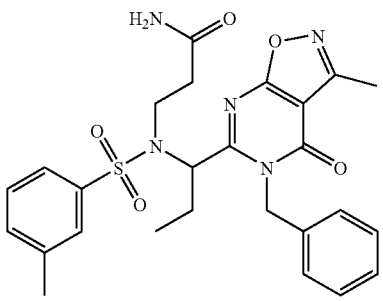

(±)-3-[[1-(5-Benzyl-3-methyl-4-oxo-4,5-dihydro-isoxazolo[5,4-d]pyrimidin-6-yl)propyl]-(toluene-3-sulfonyl)-amino]-propionamide Yield: 4.4%; LC/MS 86% at 3.11 min (ESI): 524.5 (M+H)$^+$.

Example 54

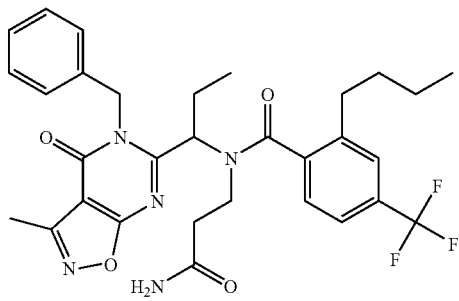

(±)-N-[1-(5-Benzyl-3-methyl-4-oxo-4,5-dihydro-isoxazolo[5,4-d]pyrimidin-6-yl)-propyl]-butyl-N-(2-carbamoyl-ethyl)-4-trifluoromethyl-benzamide Yield: 28.5%; LC/MS 91% at 3.07 min (ESI): 542.5 (M+H)+.

Example 55

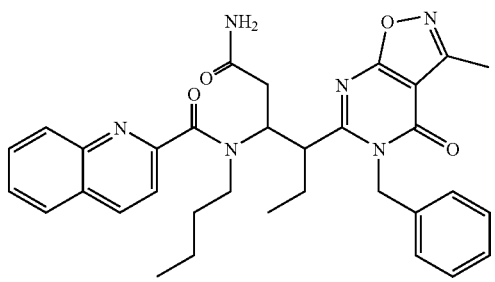

(±)-Quinoline-2-carboxylic acid [1-(5-benzyl-3-methyl-4-oxo-4,5-dihydro-isoxazolo[5,4-d]pyrimidin-6-yl)-propyl]-butyl-N-(2-carbamoyl-ethyl)-amide Yield: 21.5%; LC/MS 73% at 3.11 min (ESI): 525.5 (M+H)+.

Example 56

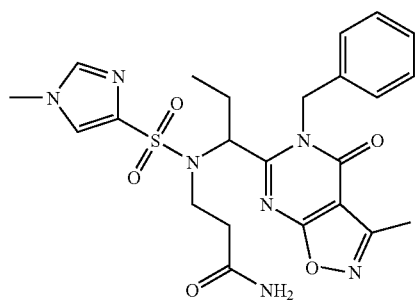

(±)-3-[[1-(5-Benzyl-3-methyl-4-oxo-4,5-dihydro-isoxazolo[5,4-d]pyrimidin-6-yl)-propyl]-(1-methyl-1H-imidazole-4-sulfonyl)-amino]-propionamide Yield: 5.6%; LC/MS 93% at 2.57 min (ESI): 514.5 (M+H)+.

Example 57

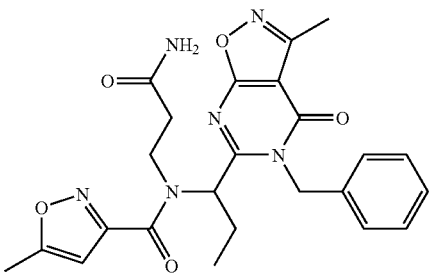

(±)-5-methyl-isoxazole-3-carboxylic acid [1-(5-Benzyl-3-methyl-4-oxo-4,5-dihydro-isoxazolo[5,4-d]pyrimidin-6-yl)-propyl]-(1-methyl-1H-imidazole-4-sulfonyl)-amino]-amide Yield: 25.9%; LC/MS 79% at 2.71 min (ESI): 479.5 (M+H)+.

Example 58

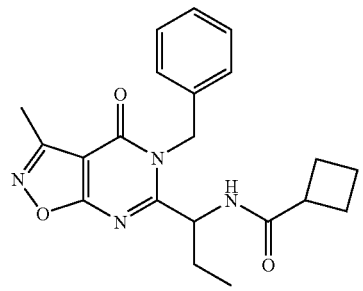

(±)-Cyclobutanecarboxylic acid [1-(5-benzyl-3-methyl-4-oxo-4,5-dihydro-isoxazolo[5,4-d]pyrimidin-6-yl)-propyl]-amide Yield: 12.8%; LC/MS 87% at 2.84 min (ESI): 452.5 (M+H)+.

Example 59

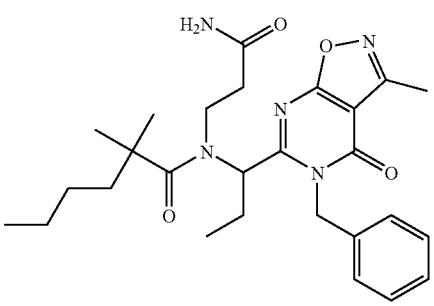

(±)-N-[1-(5-Benzyl-3-methyl-4-oxo-4,5-dihydro-isoxazolo[5,4-d]pyrimidin-6-yl)-propyl]-butyl-N-(2-carbamoyl-ethyl)-isobutyramide Yield: 3.0%; LC/MS 71% at 2.77 min (ESI): 440.6 (M+H)+.

Example 60

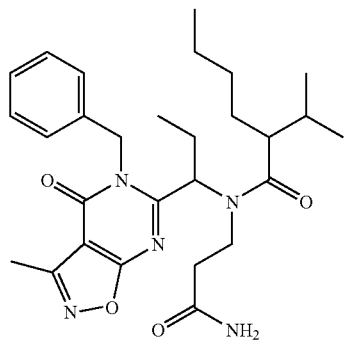

(±)-N-[1-(5-Benzyl-3-methyl-4-oxo-4,5-dihydro-
isoxazolo[5,4-d]pyrimidin-6-yl)-propyl]-butyl-N-(2-
carbamoyl-ethyl)-3-methyl-butyramide Yield: 6.5%; LC/MS 97% at 2.91 min (ESI): 454.6 (M+H)$^+$.

Example 61

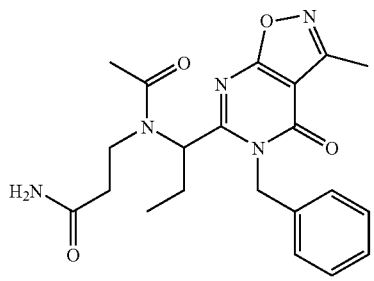

(±)-3-{Acetyl-[1-(5-benzyl-3-methyl-4-oxo-4,5-
dihydro-isoxazolo[5,4-d]pyrimidin-6-yl)-propyl]-
amino}-propionamide Yield: 3.5%; LC/MS 88% at 2.48 min (ESI): 412.5 (M+H)$^+$.

Example 62

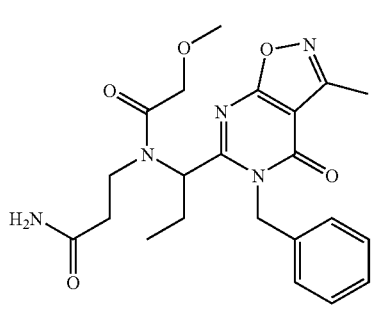

(±)-3-[[1-(5-Benzyl-3-methyl-4-oxo-4,5-dihydro-
isoxazolo[5,4-d]pyrimidin-6-yl)-propyl]-(2-meth-
oxy-acetyl)-amino]-propionamide Yield: 9.7%; LC/MS 85% at 2.48 min (ESI): 442.5 (M+H)$^+$.

Example 63

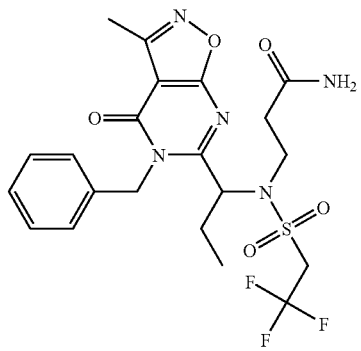

(±)-3-[[1-(5-Benzyl-3-methyl-4-oxo-4,5-dihydro-
isoxazolo[5,4-d]pyrimidin-6-yl)-propyl]-(2,2,2-trif-
luoro-ethanesulfonyl)-amino]-propionamide Yield: 6.5%; LC/MS 76% at 2.82 min (ESI): 516.5 (M+H)$^+$.

Example 64

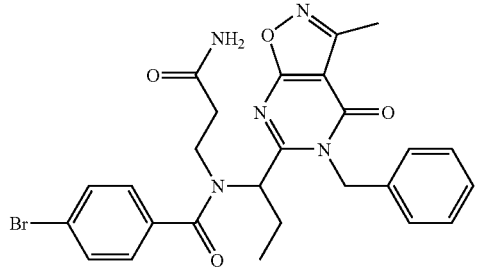

(±)-N-[1-(5-Benzyl-3-methyl-4-oxo-4,5-dihydro-
isoxazolo[5,4-d]pyrimidin-6-yl)-propyl]-4-bromo-N-
(2-carbamoyl-ethyl)-benzamide Yield: 12.8%; LC/MS 91% at 3.03 min (ESI): 552.4 (M+H)$^+$.

Examples 65 through 98 were prepared in parallel from product of Example 1 Step 5 according to the methods of Example 1 Steps 6 and 7.

Example 65

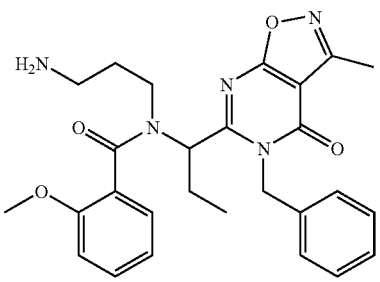

(±)-N-(3-Amino-propyl)-N-[1-(5-benzyl-3-methyl-4-
oxo-4,5-dihydro-isoxazolo[5,4-d]pyrimidin-6-yl)-
propyl]-2-methoxy-benzamide Yield: 5.9%; LC/MS 84.2% at 2.81 min (ESI): 490.3 (M+H)$^+$.

Example 66

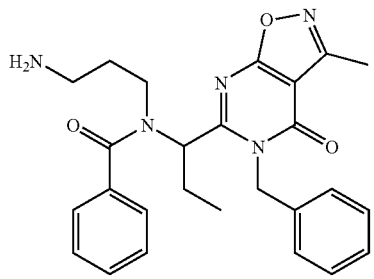

(±)-N-(3-Amino-propyl)-N-[1-(5-benzyl-3-methyl-4-oxo-4,5-dihydro-isoxazolo[5,4-d]pyrimidin-6-yl)-propyl]-benzamide Yield: 4.8%; LC/MS 96.3% at 2.79 min (EST): 460.3 (M+H)$^+$.

Example 67

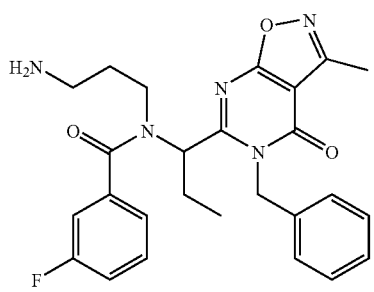

(±)-N-(3-Amino-propyl)-N-[1-(5-benzyl-3-methyl-4-oxo-4,5-dihydro-isoxazolo[5,4-d]pyrimidin-6-yl)-propyl]-3-fluoro-benzamide Yield: 5.4%; LC/MS 100% at 2.81 min (ESI): 478.4 (M+H)$^+$.

Example 68

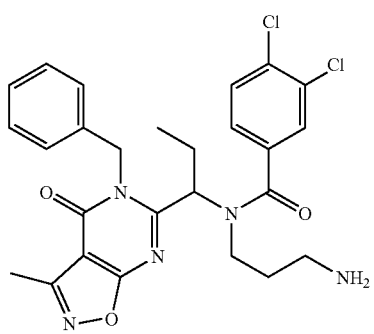

(±)-N-(3-Amino-propyl)-N-[1-(5-benzyl-3-methyl-4-oxo-4,5-dihydro-isoxazolo[5,4-d]pyrimidin-6-yl)-propyl]-3,4-dichloro-benzamide Yield: 5.1%; LC/MS 100% at 3.16 min (EST): 528.2 (M+H)$^+$.

Example 69

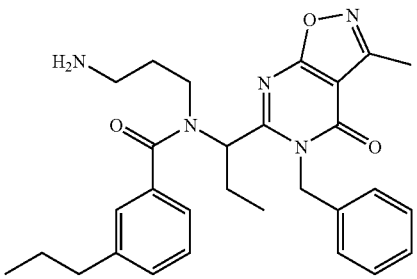

(±)-N-(3-Amino-propyl)-N-[1-(5-benzyl-3-methyl-4-oxo-4,5-dihydro-isoxazolo[5,4-d]pyrimidin-6-yl)-propyl]-3-propyl-benzamide Yield: 6.4%; LC/MS 71% at 3.25 min (ESI): 502.4 (M+H)$^+$.

Example 70

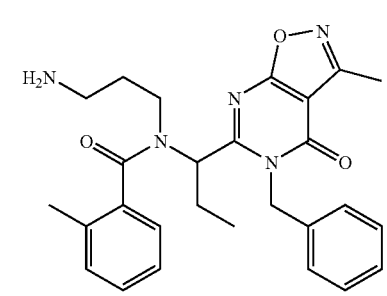

(±)-N-(3-Amino-propyl)-N-[1-(5-benzyl-3-methyl-4-oxo-4,5-dihydro-isoxazolo[5,4-d]pyrimidin-6-yl)-propyl]-2-methyl-benzamide Yield: 5.8%; LC/MS 89.8% at 2.88 min (ESI): 474.4 (M+H)$^+$.

Example 71

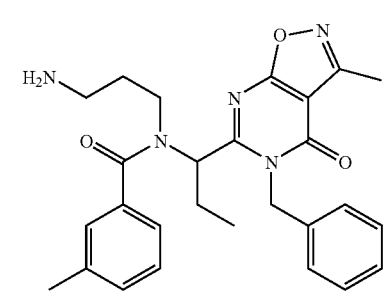

(±)-N-(3-Amino-propyl)-N-[1-(5-benzyl-3-methyl-4-oxo-4,5-dihydro-isoxazolo[5,4-d]pyrimidin-6-yl)-propyl]-3-methyl-benzamide Yield: 6.0%; LC/MS 100% at 2.94 min (ESI): 474.3 (M+H)$^+$.

Example 72

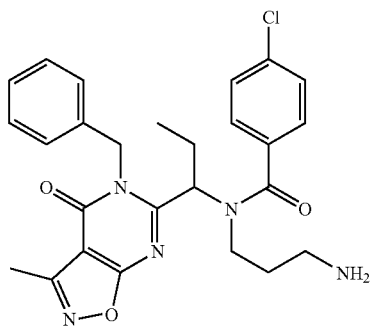

(±)-N-(3-Amino-propyl)-N-[1-(5-benzyl-3-methyl-4-oxo-4,5-dihydro-isoxazolo[5,4-d]pyrimidin-6-yl)-propyl]-4-chloro-benzamide Yield: 6.4%; LC/MS 73% at 2.88 min (ESI): 494.4 (M+H)$^+$.

Example 73

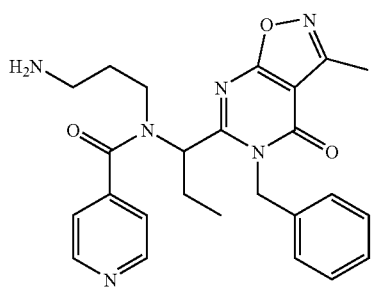

(±)-N-(3-Amino-propyl)-N-[1-(5-benzyl-3-methyl-4-oxo-4,5-dihydro-isoxazolo[5,4-d]pyrimidin-6-yl)-propyl]-isonicotinamide Yield: 11.2%; LC/MS 100% at 2.29 min (ESI): 461.4 (M+H)$^+$.

Example 74

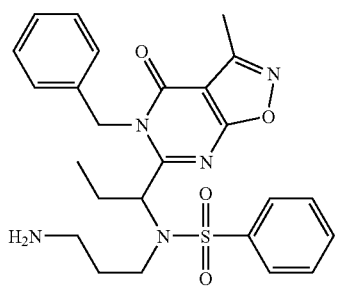

(±)-N-(3-Amino-propyl)-N-[1-(5-benzyl-3-methyl-4-oxo-4,5-dihydro-isoxazolo[5,4-d]pyrimidin-6-yl)-propyl]-benzenesulfonamide Yield: 1.6%; LC/MS 93% at 2.90 min (ESI): 496.3 (M+H)$^+$.

Example 75

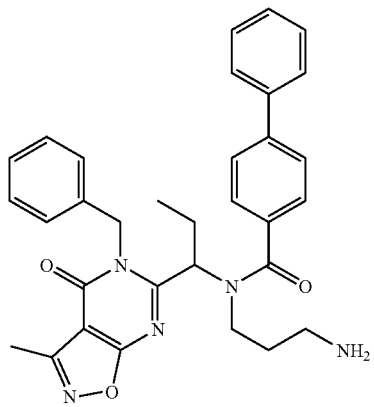

(±)-Biphenyl-4-carboxylic acid (3-amino-propyl)-[1-(5-benzyl-3-methyl-4-oxo-4,5-dihydro-isoxazolo[5,4-d]pyrimidin-6-yl)-propyl]-amide Yield: 0.7%; LC/MS 98.2% at 3.12 min (ESI): 536.5 (M+H)$^+$.

Example 76

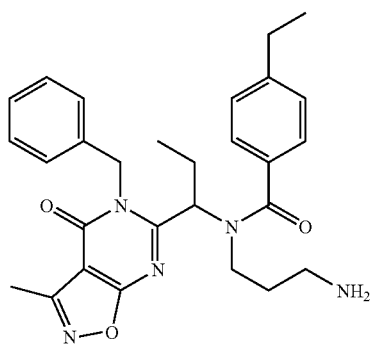

(±)-N-(3-Amino-propyl)-N-[1-(5-benzyl-3-methyl-4-oxo-4,5-dihydro-isoxazolo[5,4-d]pyrimidin-6-yl)-propyl]-4-ethyl-benzamide Yield: 5.3%; LC/MS 78.5% at 3.05 min (ESD): 488.4 (M+H)$^+$.

Example 77

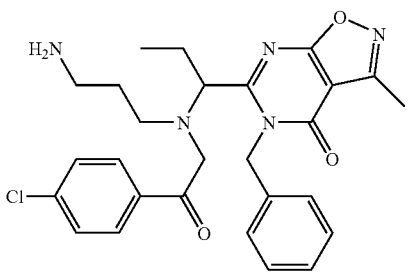

(±)-6-(1-{(3-Amino-propyl)-[2-(4-chloro-phenyl)-2-oxo-ethyl]-amino}-propyl)-5-benzyl-3-methyl-5H-isoxazolo[5,4-d]pyrimidin-4-one Yield: 2.7%; LC/MS 100% at 3.11 min (ESI): 508.4 (M+H)$^+$.

Example 78

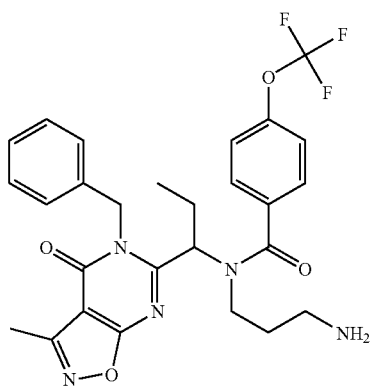

(±)-N-(3-Amino-propyl)-N-[1-(5-benzyl-3-methyl-4-oxo-4,5-dihydro-isoxazolo[5,4-d]pyrimidin-6-yl)-propyl]-4-trifluoromethoxy-benzamide Yield: 3.1%; LC/MS 80% at 3.10 min (ESI): 544.4 (M+H)+.

Example 79

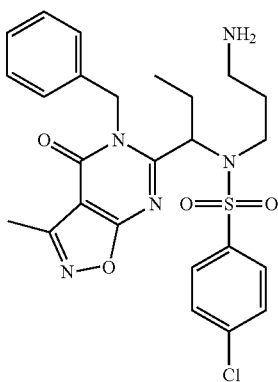

(±)-N-(3-Amino-propyl)-N-[1-(5-benzyl-3-methyl-4-oxo-4,5-dihydro-isoxazolo[5,4-d]pyrimidin-6-yl)-propyl]-4-chloro-benzenesulfonamide Yield: 1.6%; LC/MS 92.7% at 3.10 min (ESI): 530.3 (M+H)+.

Example 80

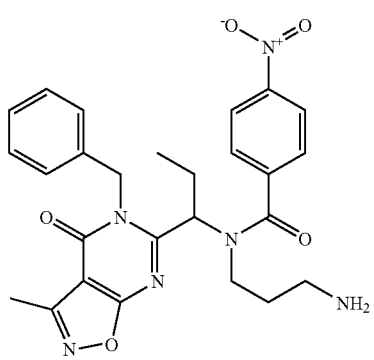

(±)-N-(3-Amino-propyl)-N-[1-(5-benzyl-3-methyl-4-oxo-4,5-dihydro-isoxazolo[5,4-d]pyrimidin-6-yl)-propyl]-4-nitro-benzamide Yield: 3.1%; LC/MS 89% at 2.70 min (ESI): 505.4 (M+H)+.

Example 81

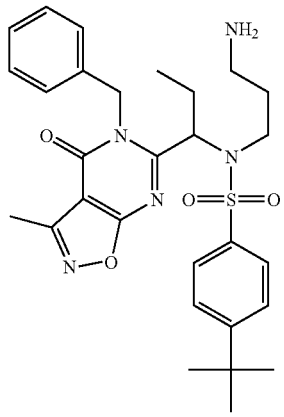

(±)-N-(3-Amino-propyl)-N-[1-(5-benzyl-3-methyl-4-oxo-4,5-dihydro-isoxazolo[5,4-d]pyrimidin-6-yl)-propyl]-4-tert-butyl-benzenesulfonamide Yield: 4.5%; LC/MS 91.8% at 3.39 min (ESI): 552.5 (M+H)+.

Example 82

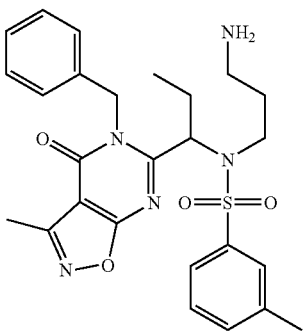

(±)-N-(3-Amino-propyl)-N-[1-(5-benzyl-3-methyl-4-oxo-4,5-dihydro-isoxazolo[5,4-d]pyrimidin-6-yl)-propyl]-3-methyl-benzenesulfonamide Yield: 1.9%; LC/MS 95.1% at 3.05 min (ESI): 510 (M+H)+.

Example 83

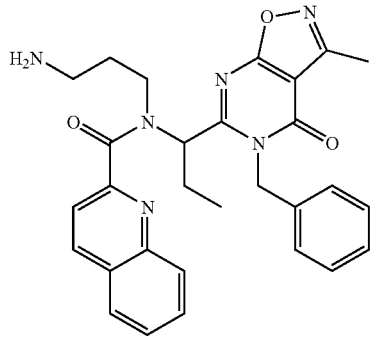

(±)-Quinoline-2-carboxylic acid (3-amino-propyl)-[1-(5-benzyl-3-methyl-4-oxo-4,5-dihydro-isoxazolo[5,4-d]pyrimidin-6-yl)-propyl]-amide Yield: 3.7%; LC/MS 91.5% at 3.08 min (ESI): 511 (M+H)+.

Example 84

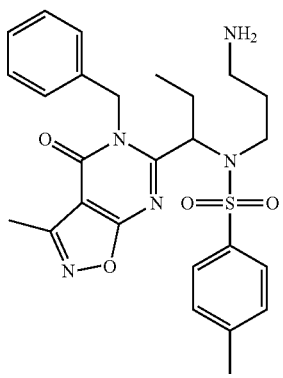

(±)-N-(3-Amino-propyl)-N-[1-(5-benzyl-3-methyl-4-oxo-4,5-dihydro-isoxazolo[5,4-d]pyrimidin-6-yl)-propyl]-4-methyl-benzenesulfonamide Yield: 5.9%; LC/MS 92% at 3.03 min (ESI): 510 (M+H)+.

Example 85

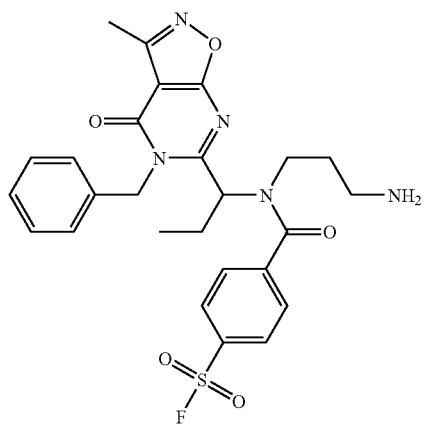

(±)-4-{(3-Amino-propyl)-N-[1-(5-benzyl-3-methyl-4-oxo-4,5-dihydro-isoxazolo[5,4-d]pyrimidin-6-yl)-propyl]-carbamoyl}-benzenesulfonyl fluoride Yield: 2.6%; LC/MS 82.8% at 2.84 min (ESI): 542 (M+H)+.

Example 86

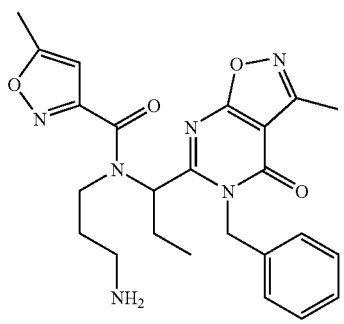

(±)-5-methyl-isoxazole-3-carboxylic acid (3-amino-propyl)-[1-(5-benzyl-3-methyl-4-oxo-4,5-dihydro-isoxazolo[5,4-d]pyrimidin-6-yl)-propyl]-amide Yield: 25.5%; LC/MS 86.4% at 2.72 min (ESI): 465 (M+H)+.

Example 87

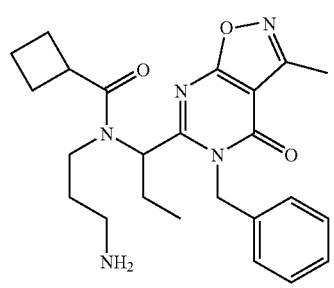

(±)-Cyclobutanecarboxylic acid (3-amino-propyl)-[1-(5-benzyl-3-methyl-4-oxo-4,5-dihydro-isoxazolo[5,4-d]pyrimidin-6-yl)-propyl]-amide Yield: 4.5%; LC/MS 100% at 2.77 min (ESI): 438 (M+H)+.

Example 88

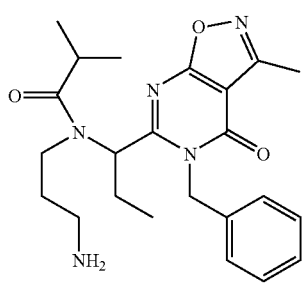

(±)-N-(3-Amino-propyl)-N-[1-(5-benzyl-3-methyl-4-oxo-4,5-dihydro-isoxazolo[5,4-d]pyrimidin-6-yl)-propyl]-isobutyramide Yield: 3.2%; LC/MS 90.4% at 2.73 min (ESI): 426 (M+H)+.

Example 89

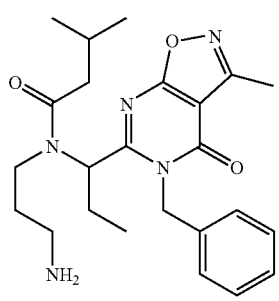

(±)-N-(3-Amino-propyl)-N-[1-(5-benzyl-3-methyl-4-oxo-4,5-dihydro-isoxazolo[5,4-d]pyrimidin-6-yl)-propyl]-3-methyl-butyramide Yield: 2.4%; LC/MS 100% at 2.94 min (ESI): 440 (M+H)+.

Example 90

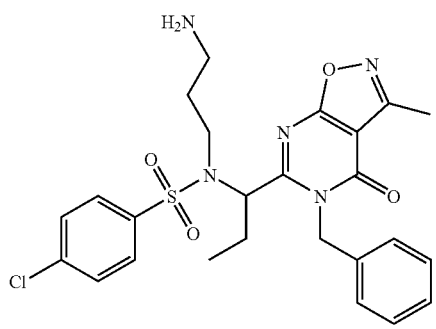

(±)-N-(3-Amino-propyl)-N-[1-(5-benzyl-3-methyl-4-oxo-4,5-dihydro-isoxazolo[5,4-d]pyrimidin-6-yl)-acetamide Yield: 14.7%; LC/MS 100% at 2.53 min (ESI): 440 (M+H)$^+$.

Example 91

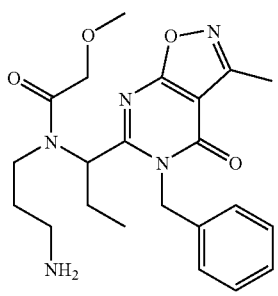

(±)-N-(3-Amino-propyl)-N-[1-(5-benzyl-3-methyl-4-oxo-4,5-dihydro-isoxazolo[5,4-d]pyrimidin-6-yl)-propyl]-2-methoxy-acetamide Yield: 2.4%; LC/MS 80.8% at 2.50 min (ESI): 428 (M+H)$^+$.

Example 92

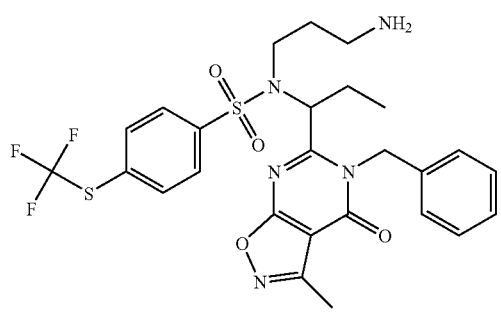

(±)-N-(3-Amino-propyl)-N-[1-(5-benzyl-3-methyl-4-oxo-4,5-dihydro-isoxazolo[5,4-d]pyrimidin-6-yl)-propyl]-4-trifluoromethylsulfanyl-benzenesulfonamide Yield: 3.5%; LC/MS 87.6% at 3.25 min (ESI): 560 (M+H)$^+$.

Example 93

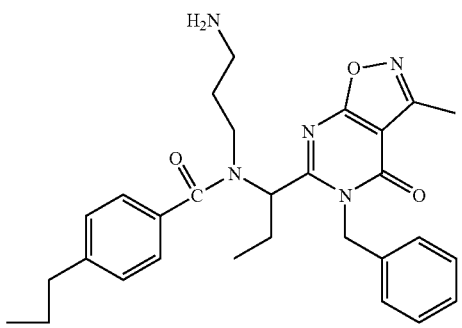

(±)-2,2,2-Trifluoro-ethanesulfonic acid (3-Amino-propyl)-[1-(5-benzyl-3-methyl-4-oxo-4,5-dihydro-isoxazolo[5,4-d]pyrimidin-6-yl)-amide Yield: 2.6%; LC/MS 88.2% at 2.86 min (ESI): 502 (M+H)$^+$.

Example 94

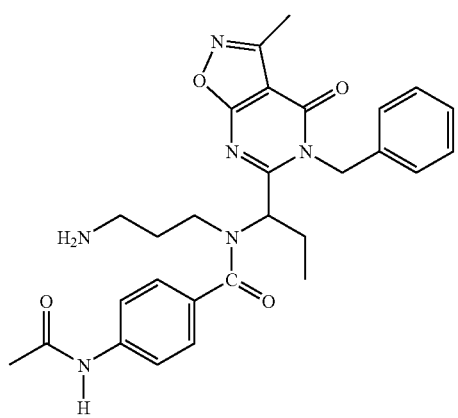

(±)-4-Acetylamino-N-(3-amino-propyl)-N-[1-(5-benzyl-3-methyl-4-oxo-4,5-dihydro-isoxazolo[5,4-d]pyrimidin-6-yl)-benzamide Yield: 2.8%; LC/MS 100% at 2.64 min (ESI): 517 (M+H)$^+$.

Example 95

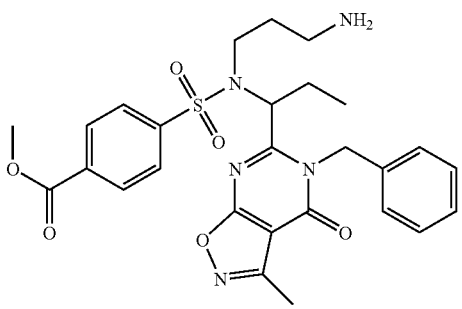

(±)-4-{(3-Amino-propyl)-[1-(5-benzyl-3-methyl-4-oxo-4,5-dihydro-isoxazolo[5,4-d]pyrimidin-6-yl)-propyl]-sulfamoyl}-benzoic acid methyl ester Yield: 0.9%; LC/MS 74.9% at 2.97 min (ESI): 518 (M+H)$^+$.

Example 96

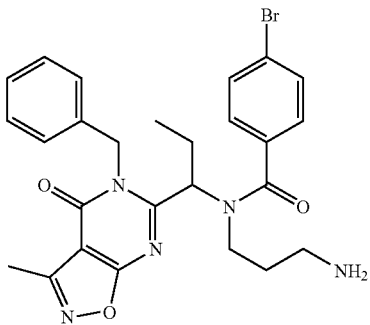

(±)-N-(3-Amino-propyl)-N-[1-(5-benzyl-3-methyl-4-oxo-4,5-dihydro-isoxazolo[5,4-d]pyrimidin-6-yl)-propyl]-4-bromo-benzamide Yield: 6.5%; LC/MS 100% at 3.15 min (ESI): 538 (M+H)$^+$.

Example 97

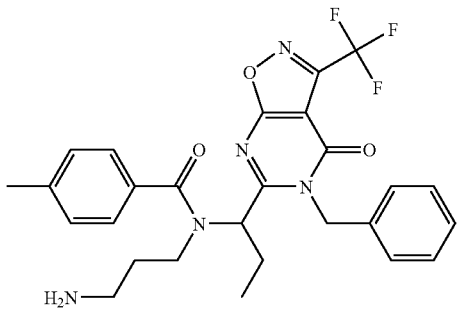

(±)-N-(3-Amino-propyl)-N-[1-(5-benzyl-4-oxo-3-trifluoromethyl-4,5-dihydro-isoxazolo[5,4-d]pyrimidin-6-yl)-propyl]-4-methyl-benzamide Step 1: 5-Amino-3-trifluoromethyl-isoxazole-4-carboxylic acid amide (7).

A solution of trifluoroacetohydroximoyl bromide etherate (17.6 g, 91.6 mmol) in 20 mL of EtOH was added to a solution of 2-cyano-acetamide (7.7 g, 91.6 mmol) and sodium ethoxide (6.2 g, 91.6 mmol) in ethanol (300 mL). After stirring at room temperature for 3 h, the solvent was removed. The residue was diluted with EtOAc and washed with water, brine, and dried over MgSO$_4$. The organic phase was filtered and concentrated to give a brown oil. The product was purified by a flash chromatography on SiO$_2$ eluting with hexanes:EtOAc (3:1) to give 7 as a light yellow solid (11 g, 40%); MS (ESI): 196 (M+H)$^+$. Ref: *J. Heterocyclic Chem.* 1535 (1986).

Step 2: [1-(4-Oxo-3-trifluoromethyl-4,5-dihydro-isoxazole[5,4-d]pyrimidin-6-yl)-propyl]-carbamic acid tert-butyl ester (8).

To a solution of 7 (3.4 g, 17.4 mmol) in EtOH (200 mL) stirred at room temperature was added NaOEt (5.9 g, 87.2 mmol), followed by 2-tert-Butoxycarbonylamino-butyric acid methyl ester (18.9 g, 87.2 mmol). The mixture was refluxed for 14 h, cooled to room temperature and concentrated in vacuo. The residue was diluted in EtOAc, washed with water, brine, dried over MgSO$_4$, and filtered. The solvent was removed, and the residue was purified by SiO$_2$ chromatography, eluting with 20%–30% heaxanes:EtOAc. Product 8 was obtained as a foam (1.1 g, 19.4%). $^1$H NMR (CDCl$_3$): δ 5.43 (m, 1H), 4.13 (m, 1H), 2.02–1.89 (m, 3H), 1.42 (s, 9H), 1.06 (t, J=7.4 Hz, 3H).

Step 3: [1-(5-Benzyl-4-oxo-3-trifluoromethyl-4,5-dihydro-isoxazole[5,4-d]pyrimidin-6-yl)-propyl]-carbamic acid tert-butyl ester (9).

To a solution of 8 (1.2 g, 3.31 mmol) in DMF (20 mL) was added solid K$_2$CO$_3$ (1.6 g, 10.9 mmol), followed by benzylbromide (1.13 g, 6.62 mmol). The reaction mixture was stirred at room temperature overnight. The mixture was diluted with EtOAc, washed with water, brine, dried, filtered and concentrated. The crude product was purified by SiO$_2$ chromatography eluting with 10%–15%–20% hexanes:EtOAc to afford 570 mg of desired product 9 (47%). $^1$H NMR (CDCl$_3$): δ 7.49–7.34 (m, 5H), 5.69 (m, 2H), 5.47 (m, 1H), 4.91 (m, 1H), 2.00 (m, 1H), 1.80 (m, 2H), 1.46 (s, 9H), 0.929 (t, J=7.2 Hz, 3H).

Step 4: 6-(1-Amino-propyl)-5-benzyl-3-trifluoromethyl-5H-isoxazolo[5,4-d]pyrimidin-4-one (10).

To a solution of 9 (160 mg, 0.358 mmol) in CH$_2$Cl$_2$ (4 mL) was added TFA (1 mL). The reaction mixture was stirred at room temperature for 30 minutes. The solvent was removed in vacuo to afford 10 pure enough for the next step. $^1$H NMR (CDCl$_3$): δ 7.35–7.18 (m, 5H), 5.67 (d, J=15.9 Hz, 1H), 5.18 (d, J=15.9 Hz, 1H), 4.71 (m, 1H), 1.72–1.65 (m, 1H), 1.55–1.51 (m, 2H), 0.79 (t, J=7.2 Hz, 1H).

Step 5: (±)-{3-[1-(5-Benzyl-4-oxo-3-trifluoromethyl-4,5-dihydro-isoxazolo[5,4-d]pyrimidin-6yl)-propylamino]-propyl}-carbamic acid tert-butyl ester (11).

To a solution of 10 (0.358 mmol) in MeOH (5.0 mL) was added (3-oxo-propyl)-carbamic acid tert-butyl ester (116 mg, 0.671 mmol), followed by NaBH(OAc)$_3$ (142 mg, 0.671 mmol). The reaction mixture was stirred at room temperature for 3 h. Water was added to quench the reaction, the aqueous phase was extracted with EtOAc three times. The combined organic phases were washed with brine, dried over MgSO$_4$, filtered and concentrated. The residue was purified by SiO$_2$ chromatography (EtOAc:heaxanes/1:2) to give 11 (120 mg, 53%). $^1$H NMR (CDCl$_3$): δ 7.35–7.18 (m, 5H), 5.67 (d, J=15.9 Hz, 1H), 5.18 (d, J=15.9 Hz, 1H), 7.47–7.34 (m, 5H), 5.73–5.66 (m, 2H), 5.48–5.46 (m, 1H), 4.92–4.91 (m, 1H), 2.02–1.80 (m, 2H), 1.46 (s, 9H), 0.92 (t, J=7.14 Hz, 3H).

Step 6: (±)-{3-[[1-(5-Benzyl-4-oxo-3-trifluoromethyl-4,5-dihydro-isoxazolo[5,4-d]pyrimidin-6yl)-propyl]-(4-methyl-benzoyl)-amino]-propyl}-carbamic acid tert-butyl ester (12).

To a solution of 11 (60 mg, 0.118 mmol) in CH$_2$Cl$_2$ (2.0 mL) stirred at room temperature was added 4-methyl-benzoyl chloride (24.1 mg, 0.153 mmol), followed by Et$_3$N (18 mg, 0.117 mmol). The reaction mixture was stirred at room temperature for 1 h. More 4-methyl-benzoyl chloride (24 mg, 0.153 mmol), and Et$_3$N (18 mg, 0.117 mmol) were added. After another hour, the reaction mixture was purified by SiO$_2$ chromatography directly (EtOAc:heaxanes/1:4) to afford 12 (52 mg, 70%). MS (ESI): 628 (M+H)$^+$.

Step 7: (±)-N-(3-Amino-propyl)-N-[1-(5-benzyl-4-oxo-3-trifluoromethyl-4,5-dihydro-isoxazolo[5,4-d]pyrimidin-6-yl)-propyl]-4-methyl-benzamide (13).

To a solution of 12 (52 mg, 0.083 mmol) in CH$_2$Cl$_2$ (4.0 mL) stirred at room temperature was added TFA (1.0 mL). The reaction mixture was stirred at room temperature for 30 min. Solvent was removed in vacuo, the residue was purified by preparative HPLC to give 13 as a white solid (42 mg, 96%). MS (ESI): 528 (M+H)$^+$.

Compounds in the Examples 98 through 101 were prepared following the similar procedures described in Scheme 2 and Example 97.

Example 98

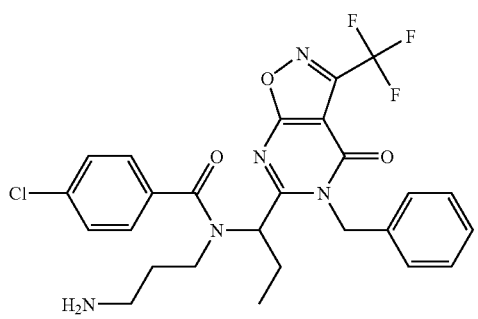

(±)-N-(3-Amino-propyl)-N-[1-(5-benzyl-4-oxo-3-trifluoromethyl-4,5-dihydro-isoxazolo[5,4-d]pyrimidin-6-yl)-propyl]-4-chloro-benzamide

MS (ESI): 548 (M+H)$^+$.

Example 99

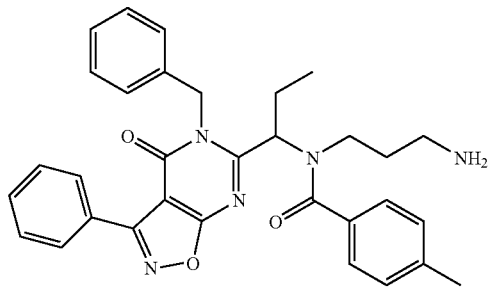

(±)-N-(3-Amino-propyl)-N-[1-(5-benzyl-4-oxo-3-phenyl-4,5-dihydro-isoxazolo[5,4-d]pyrimidin-6-yl)-propyl]-4-methyl-benzamide

MS (ESI): 536 (M+H)$^+$.

Example 100

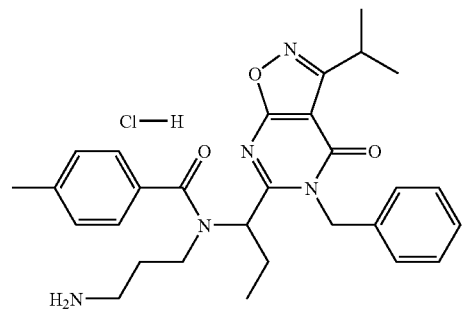

(±)-N-(3-Aminopropyl)-N-[1-(5-benzyl-3-isopropyl-4-oxo-4,5-dihydroisoxazolo[5,4-d]pyrimidin-6-yl)-propyl]-4-methylbenzamide Hydrochloride $^1$H NMR (DMSO-d$_6$): δ 7.73 (br s, 2H), 71.9–7.26 (m, 3H), 7.17 (d, J=7.7 Hz, 2H), 7.12 (d, J=7.7 Hz, 2H), 6.95 (br s, 2H), 5.68 (d, J=16.5 Hz, 1H), 5.46 (br s, 1H), 4.81 (br d, J=15.4 Hz, 1H), 3.23–3.34 (m, 3H), 2.36–2.43 (m, 2H), 2.28 (s, 3H), 1.94–2.04 (m, 1H), 1.77–1.87 (m, 1H), 1.60–1.70 (m, 1H), 1.42–1.52 (m, 1H), 1.32 (d, J=6.6 Hz, 6H), 0.57 (t, J=7.4 Hz, 3H); $^{13}$C NMR (DMSO-d6): δ 172.8, 171.3, 165.7, 161.7, 156.9, 139.0, 135.2, 132.7, 128.6, 128.1, 127.0, 125.9, 125.6, 99.0, 98.5, 45.3, 41.2, 36.4, 27.5, 26.4, 24.1, 20.4, 19.54, 19.50, 9.7; HRMS: 502.2818 (M+H)$^+$.

Example 101

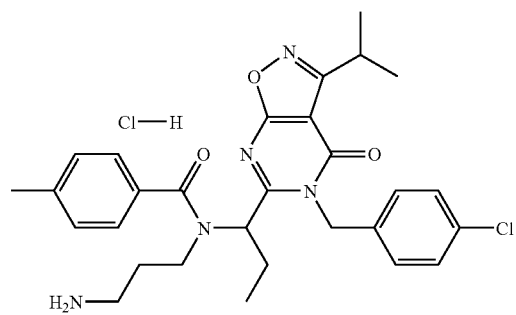

(±)-N-(3-Aminopropyl)-N-{1-[5-(4-chlorobenzyl)-3-isopropyl-4-oxo-4,5-dihydroisoxazolo[5,4-d]pyrimidin-6-yl]-propyl}-4-methylbenzamide Hydrochloride $^1$H NMR (DMSO-d$_6$, at 100° C.): δ 7.69 (br s, 2H), 7.35 (d, J=8.2 Hz, 2H), 7.23 (d, J=8.2 Hz, 2H), 7.17 (d, J=7.7 Hz, 2H), 7.08 (br s, 2H), 5.66 (d, J=16.5 Hz, 1H), 5.51 (br s, 1H), 4.94 (br s, 1H), 3.28–3.42 (m, 3H), 3.42–3.54 (m, 2H), 2.35 (s, 3H), 2.06–2.17 (m, 1H), 1.85–1.98 (m, 1H), 1.66–1.77 (m, 1H), 1.47–1.60 (m, 1H), 1.39 (d, J=7.2 Hz, 6H), 0.70 (t, J=7.2 Hz, 3H); HRMS: 536.2431 (M+H)$^+$.

Example 102

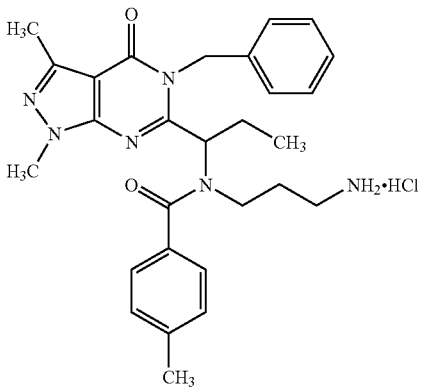

(±)-1,3-Dimethyl-5-benzyl-6-[2-(N-aminopropyl-N-toluoylamino)propyl]pyra-[1,2]-zolodihydropyrimidinone hydrochloride Step 1: 1,3-Dimethyl-5-amino-4-cyanopyrazole (14).

To a solution of methylhydrizine (5 mL, 94 mmole) in 16 mL of water was added 2-methyl-2-ethoxyethylenedinitrile (5.10 g, 94 mmole) in portions at −5° C. under $N_2$. The mixture was stirred at room temperature overnight. The precipitated white solid was collected, washed with water and dried as pure titled product (3.85 g, 30%). $^1$H NMR (DMSO-$d_6$): δ 6.43 (s, 2H), 3.42 (s, 3H), 2.03 (s, 3H).

Step 2: 1,3-Dimethyl-6-propylpyra[1,2]zolodihydropyrimidinone (15).

To a stirred mixture of 1,3-Dimethyl-5-amino-4-cyanopyrazole (3.2 g, 23.5 mmole) and butyric anhydride (18 mL, 110 mmole) was added concentrated sulfuric acid (1.8 mL) at 0° C. under $N_2$. After the addition, the reaction mixture was heated at 100° C. for 1 h, cooled to 0° C., added ice and stirred for 1–2 hrs. The precipitated white solid was collected, washed with water and dried to give cyclized product (1.15 g, 24%). $^1$H NMR (DMSO-$d_6$): δ 11.87 (s, 1H), 3.75 (s, 3H), 2.55 (t, J=7.7 Hz, 2H), 2.37 (s, 3H), 1.67 (m, 2H), 0.91 (t, J=7.43 Hz, 3H); MS (ESI), 207.13 (M+H)$^+$.

Step 3: 1,3-Dimethyl-5-benzyl-6-propylpyra[1,2]zolodihydropyrimidinone (16).

To a suspension of 60% NaH (0.36 g, 9.0 mmole) in THF (25 mL) was added 1,3-dimethyl-6-propylpyra[1,2]zolodihydropyrimidinone (1.0 g, 4.85 mmole) at room temperature. After stirring for 20 min, it was treated with benzylbromide (0.72 mL, 6.05 mmole) followed by sodium iodide (0.13 g, 0.87 mmole). After 20 min at room temperature, the mixture was heated at 60° C. overnight. Additional NaH (0.16 g) and benzyl bromide (0.40 mL) were added, it was heated at 60° C. overnight. Again NaH (0.16 g) and BnBr (1.0 mL) were added, and the mixture was heated at same temperature for 3 days, cooled to 0° C. and quenched with aqueous $NH_4Cl$ solution, extracted with EtOAc (3×50 mL), dried over $MgSO_4$. Concentration and purification by flash column chromatography (EtOAc/Hexane 1:4 to 1:3) gave the pure product as an oil (0.7 g, 49%). $^1$H NMR (CDCl$_3$): δ 7.31 (2H, m), 7.26 (m, 1H), 7.11 (m, 2H), 5.32 (s, 2H), 3.80 (s, 3H), 2.68 (t, J=7.7 Hz, 2H), 2.42 (s, 3H), 1.66 (m, 2H), 0.86 (t, J=7.15 Hz, 3H); $^{13}$C NMR (CDCl$_3$): δ 160.54, 159.27, 151.42, 145.87, 136.51, 128.91, 127.52, 127.42, 126.27, 101.78, 45.44, 37.13, 33.42, 20.23, 13.72, 13.53; MS (ESI): 297.18 (M+H)$^+$.

Step 4: (±)-1,3-Dimethyl-5-benzyl-6-(α-bromopropyl)pyra[1,2]zolodihydropyrimidinone (17).

A mixture of 1,3-dimethyl-5-benzyl-6-propylpyra[1,2]zolodihydropyrimidinone (0.66 g, 2.23 mmole), $Br_2$ (0.15 mL, 2.93 mmole) and NaOAc (0.99 g, 12.0 mmole) in HOAc (3.5 mL) was sealed and heated at 60° C. for 2 weeks. The mixture was cooled to room temperature, diluted with water and extracted with EtOAc (3×40 mL), the combined organic solution was washed with aqueous $NaHCO_3$ and brine, then dried over $MgSO_4$. Concentration and purification by flash column (EtOAc/Hexane 1:4) gave the product as white waxy solid (0.67 g, 80%). $^1$H NMR (CDCl$_3$): δ 7.33 (m, 2H), 7.27 (m, 1H), 7.11 (d, J=7.7 Hz, 2H), 6.20 (d, J=16.45 Hz, 1H), 4.82 (d, J=16.45 Hz, 1H), 4.62 (t, J=7.43 Hz, 1H), 3.93 (s, 3H), 2.62 (s, 3H), 2.40 (m, 1H), 2.21 (m, 1H), 0.74 (t, J=7.15 Hz, 3H); $^{13}$C NMR (CDCl$_3$): δ 158.86, 157.47, 150.88, 146.26, 136.78, 129.11, 127.82, 127.68, 125.88, 102.37, 48.77, 44.70, 33.64, 29.09, 13.47, 12.22; MS (ESI): 375, 377 (M+H)$^+$.

Step 5: (±)-1,3-Dimethyl-5-benzyl-6-{[2-(N-Boc-aminopropyl)amino)]propyl}pyra-[1,2]zolo-dihydropyrimidinone (18).

A solution of 1,3-dimethyl-5-benzyl-6-(α-bromopropyl)pyra[1,2]zolodihydropyrimidi-none (0.53 g, 1.41 mmole) and N-Boc-propyldiamine (0.7 mL, 4.0 mmole) in ethanol (30 mL) was heated at reflux overnight. The EtOH was removed in vacuo and the reaction mixture was purified by flash column chromatography (EtOAc/Hexane/MeOH 6:3.5:0.2) to give the product as an oil (0.55 g, 83%). $^1$H NMR (CDCl$_3$): δ 7.33 (m, 2H), 7.27 (m, 1H), 7.14 (d, J=7.15 Hz, 2H), 5.85 (d, J=15.4 Hz, 1H), 5.17 (m, 1H), 4.88 (m, 1H), 3.90 (s, 3H), 3.63 (m, 1H), 3.08 (m, 1H), 2.99 (m, 1H), 2.61 (s, 1H), 2.37 (m, 1H), 1.92 (m, 1H), 1.63 (m, 1H), 1.53 (m, 1H), 1.41 (s, 9H), 1.33 (m, 2H), 0.94 (t, J=7.15 Hz, 3H); $^{13}$C NMR (CDCl$_3$): δ 159.2, 156.1, 151.3, 146.1, 136.7, 129.0, 127.8, 126.5, 101.9, 61.0, 45.8, 44.7, 39.6, 33.5, 28.4, 13.5, 10.8; MS (ESI): 469 (M+H)$^+$.

Step 6: (±)-1,3-Dimethyl-5-benzyl-6-[2-(N-aminopropyl-N-toluoylamino)propyl]pyra-[1,2]-zolodihydropyrimidinone hydrochloride (20).

To a solution of 1,3-Dimethyl-5-benzyl-6-{[2-(N-Bocaminopropyl)amino)]propyl}pyra-[1,2]-zolodihydropyrimidinone (0.50 g, 1.07 mmole) and Et$_3$N (0.19 mL, 1.36 mmole) in $CH_2Cl_2$ (10 mL) was added p-toluoyl chloride (0.15 mL, 1.13 mmole) at room temperature under $N_2$. The mixture was stirred for 1 h and diluted with EtOAc (100 mL), washed with water and brine and dried with $MgSO_4$. Concentration and purification by flash column chromatography (EtOAc/Hexane 1:4) gave the product as an oil (0.55 g, 87%).

A solution of the above oil product (0.52 g, 1.07 mmole) in $CH_2Cl_2$ (5 mL) was treated with TFA (3 mL). After 30 min, excess TFA and $CH_2Cl_2$ were removed. The residue was neutralized with aqueous $NaHCO_3$ and extracted with EtOAc (2×80 mL) and dried over $MgSO_4$. Concentration and purification by preparative HPLC gave the TFA salt of the product. The TFA salt was neutralized and converted to HCl salt to provide 9 as a white solid (0.26 g, 57%). $^{13}$C NMR (CDCl$_3$): δ 173.1, 158.6,156.7, 150.4, 146.7, 142.0, 135.8, 132.3, 129.9, 128.5, 127.6, 127.1, 125.7, 102.5, 61.2, 44.1, 39.0, 37.4, 33.9, 27.5, 26.4, 21.4, 13.5, 10.2; MS (ESI): 487.48 (M+H)$^+$.

Example 103

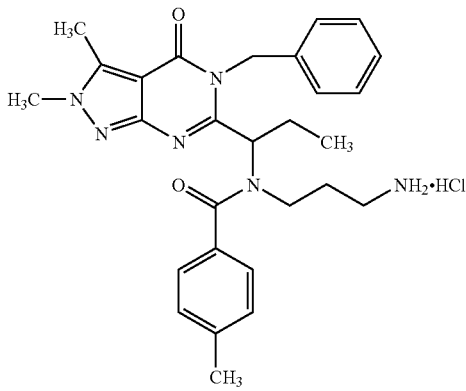

(±)-2,3-Dimethyl-5-benzyl-6-[2-(N-aminopropyl-N-toluoylamino)propyl]pyra-[1,2]-zolodihydropyrimidinone hydrochloride (27)

Step 1: 2,3-Dimethyl-5-amino-4-cyanopyrazole (21).

To a solution of NaOH (3.75 g, 93.8 mmole) in 20 mL of water at 0° C. under $N_2$ was added methylhydrizine (5 mL, 94 mmole) followed by 2-methyl-2-ethoxylethlene-dinitrile (5.10 g, 94 mmole) in portions over 5 min. After 3 h the reaction mixture was warmed to room temperature and stirred overnight. The precipitated solid was collected, washed with water and dried to provide the product as a yellow solid (3.2 g, 25%). $^1$H NMR (CDCl$_3$): δ 3.99 (s, 2H), 3.61 (s, 3H), 2.31 (s, 3H).

Step 2: 2,3-Dimethyl-6-propylpyra[1,2]zolodihydropyrimidinone (22).

To a stirred mixture of 2,3-dimethyl-5-amino-4-cyanopyrazole (3.2 g, 23.5 mmole) and butyric anhydride (18 mL, 110 mmole) was added concentrated sulfuric acid (1.8 mL) at 0° C. under $N_2$. The reaction mixture was heated at 100° C. for 3 h, cooled to 0° C., added with ice and stirred overnight. The pH of the reaction mixture was adjusted to 8–9 with 50% NaOH at 0° C. The precipitated solid was collected, washed with water and dried to give the product as a white solid (2.53 g, 52.2%). The mother liquor was washed with methylene chloride (2×200 mL, 1×100 mL), and organic solution was dried over MgSO$_4$ and concentrated to give the second crop of product (1.53 g, 31.5%, total 83.7%). $^1$H NMR (CDCl$_3$): δ 10.55 (s, 1H), 3.92 (s, 3H), 2.68 (m, 2H), 2.66 (s, 3H), 1.88 (m, 2H), 1.03 (t, J=7.44 Hz, 3H); MS (ESI), 207.15 (M+H)$^+$.

Step 3: 2,3-Dimethyl-5-benzyl-6-propylpyra[1,2]zolodihydropyrimidinone (23).

To a solution of 2,3-dimethyl-6-propylpyra[1,2]zolodihydropyrimidinone (1.38 g, 6.69 mmole) in a mixture of THF (22 mL) and DMF (15 mL) was added lithium bis(trimethylsilyl)amide in THF (1.0 N, 8.0 mL, 8.0 mmole) at room temperature under $N_2$. After stirring for 20 min, the mixture was treated with benzylbromide (1.0 mL, 8.40 mmole) followed by sodium iodide (0.15 g, 1.0 mmole) and it was stirred at room temperature overnight. The reaction mixture was quenched with aqueous NH$_4$Cl solution, extracted with EtOAc (3×80 mL). The EtOAc solution was washed with 10% aqueous LiCl solution three times, dried over MgSO$_4$, concentrated and purified by flash column on silica gel (EtOAc/Hexane/MeOH 9:1:0 to 9:0:1) to give the product as a white solid (0.65 g, 33%). $^1$H NMR (CDCl$_3$): δ 7.31 (2H, m), 7.24 (m, 1H), 7.13 (d, J=7.15 Hz, 2H), 5.32 (s, 2H), 3.92 (s, 3H), 2.68 (s, 3H), 2.65 (t, J=7.67 Hz, 2H), 1.81 (m, 2H), 0.95 (t, J=7.42 Hz, 3H); $^{13}$C NMR (CDCl$_3$): δ 160.68, 159.35, 156.85, 139.52, 136.88, 128.85, 127.38, 126.11, 103.03, 45.20, 37.03, 36.65, 20.11, 13.76, 10.97; MS (ESI), 297.14 (M+H)$^+$.

Step 4: (±)-2,3-Dimethyl-5-benzyl-6-(α-bromopropyl)pyra[1,2]zolodihydropyrimidinone (24).

A mixture of 2,3-dimethyl-5-benzyl-6-propylpyra[1,2]zolodihydropyrimidinone (0.63 g, 2.12 mmole), bromine (0.14 mL, 2.73 mmole) and NaOAc (1.01 g, 12.3 mmole) in HOAc (3.5 mL) was heated in a sealed tube at 60° C. overnight. The mixture was cooled to room temperature, added with water and the solid was collected by filtration which was washed with water to obtain product as an yellow solid after drying (0.71 g, 89%). $^1$H NMR (CDCl$_3$): δ 7.32 (m, 2H), 7.25 (m, 1H), 7.10 (d, J=7.15 Hz, 2H), 6.14 (d, J=17.05 Hz, 1H), 4.84 (d, J=16.45 Hz, 1H), 4.56 (t, J=7.15 Hz, 1H), 3.95 (s, 3H), 2.71 (s, 3H), 2.50 (m, 1H), 2.21 (m, 1H), 0.73 (t, J=7.43 Hz, 3H); $^{13}$C NMR (CDCl$_3$): δ 160.33, 156.53, 156.28, 140.03, 137.07, 129.05, 127.67, 125.73, 102.01, 49.26, 44.42, 36.84, 29.12, 12.31, 10.98; MS (ESI), 375.10, 377.04 (M+H)$^+$.

Step 5: (±)-2,3-Dimethyl-5-benzyl-6-{[2-(N-Bocaminopropyl)amino)]propyl}pyra-[1,2]zolo-dihydropyrimidinone (25).

A solution of 2,3-dimethyl-5-benzyl-6-(α-bromopropyl)pyra[1,2]zolodihydropyrimidi-none (0.65 g, 1.73 mmole) and N-Boc-propyldiamine (0.75 mL, 4.3 mmole) in ethanol (28 mL) was heated at reflux temperature for 20 h. After removing the solvent in vacuo the residue was purified by flash column chromatography on silica gel (EtOAc/Hexane/MeOH 6:3:0.2) to give the product as a glassy solid (0.68 g, 84%). $^1$H NMR (CDCl$_3$): δ 7.31 (m, 2H), 7.26 (m, 1H), 7.13 (m, 2H), 5.83 (m, 1H), 5.39 (m, 1H), 4.80 (m, 1H), 3.94 (s, 3H), 3.54 (m, 1H), 3.08 (m, 1H), 2.96 (m, 1H), 2.71 (s, 1H), 2.44 (m, 1H), 1.82 (m, 1H), 1.63 (m, 1H), 1.53 (m, 1H), 1.41 (s, 9H), 1.27 (m, 2H), 0.96 (t, J=6.82 Hz, 3H); $^{13}$C NMR (CDCl$_3$): δ 162.60, 160.62, 156.71, 155.94, 139.94, 137.0, 128.95, 126.33, 103.15, 78.67, 60.92, 46.13, 44.77, 39.80, 36.71, 29.33, 29.15, 28.44, 10.99; MS (ESI), 469.33 (M+H)$^+$.

Step 6: (±)-2,3-Dimethyl-5-benzyl-6-[2-(N-aminopropyl-N-toluoylamino)propyl]pyra-[1,2]-zolodihydropyrimidinone hydrochloride.

To a solution of 2,3-dimethyl-5-benzyl-6-{[2-(N-Boc-aminopropyl)amino)]propyl}pyra-[1,2]-zolodihydropyrimidinone (0.63 g, 1.34 mmole) and Et$_3$N (0.24 mL, 1.72 mmole) in CH$_2$Cl$_2$ (15 mL) was added with p-toluoyl chloride (0.19 mL, 1.43 mmole) at room temperature under $N_2$. The mixture was stirred for 2 h, mostly concentrated and the residue was washed with water and dried to give an oily product 26 (0.79 g, 99%).

To a solution of the above product (0.74 g, 1.26 mmole) in CH$_2$Cl$_2$ (8 mL) was added TFA (4 mL). After 30 min. the mixture was mostly concentrated and the residue was neutralized with aqueous NaHCO$_3$ solution, extracted with EtOAc (3×50 mL), dried over MgSO$_4$, and concentrated to obtain an amine as an oil. The free amine was converted to HCl salt by mixing with 1N aqueous HCl solution and lyophilized to obtain the final HCl salt product as a white solid of Example 103 (27) (0.65 g, 99%). $^{13}$C NMR (DMSO-d$_6$): δ 171.5, 159.7, 155.6, 155.4, 140.4, 139.1, 137.4, 133.3, 129.2, 128.8, 127.3, 126.0, 126.1, 102.2, 56.0, 44.2, 41.7, 36.8, 36.6, 28.3, 26.9, 24.4, 21.1, 10.8; MS (ESI), 487.30 (M+H)$^+$.

Example 104

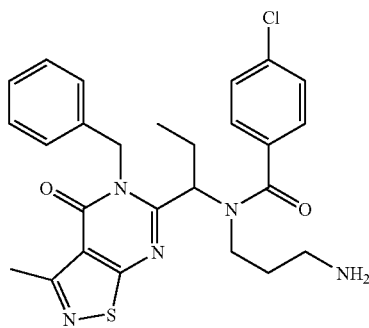

(±)-N-(3-Amino-propyl)-N-[1-(5-benzyl-3-methyl-4-oxo-4,5-dihydro-isothiazolo[5,4-d]pyrimidin-6-yl)-propyl]-4-chloro-benzamide (35)

Step 1: 5-amino-3-methyl-isothiazole-4-carboxylic acid amide (29).

Compound 28 (4.0 g, 29 mmol) was dissolved in concentrated H$_2$SO$_4$ (20 mL). The reaction mixture was heated at 70° C. for 2 h, then cooled to room temperature, and poured into ice water. The pH was adjusted to 8 by slowly adding saturated NH$_4$OH. The solid product was collected by filtration, dried under vacuum overnight to give 29 (3.0 g, 66%). $^1$H-NMR (400 MHz, DMSO-d$_6$): δ 7.51 (s, 2H), 6.88 (brs, 2H), 2.39 (s, 3H).

Step 2: 3-methyl-6-propyl-5H-isothiazolo[5,4-d]pyrimidin-4-one (30).

A mixture of 29 (3.0 g, 19.1 mmol), trimethyl orthobutyrate (7.0 mL) in acetic anhydride (7.0 mL) was heated at 130° C. in an open flask for 3 h, then cooled to room temperature and poured into ice water. The mixture was extracted with EtOAc for 3 times. The combined organic layers were dried over Na$_2$SO$_4$, filtered and concentrated. The residue was purified by silica gel column chromatography to give 30 (1.6 g, 40%) as a yellow solid. $^1$H-NMR (400 MHz, CDCl$_3$): δ 12.15 (brs, 1H), 2.81 (s, 3H), 2.78 (t, J=7.68 Hz, 2H), 1.90 (m, 2H), 1.07 (t, J=7.37 Hz, 3H).

Step 3: 5-benzyl-3-methyl-6-propyl-5H-isothiazolo[5,4-d]pyrimidin-4-one (31).

To a solution of 30 (730 mg, 3.5 mmol) in dioxane (10 mL) was added BnBr (830 μl, 7 mmol) and Cs$_2$CO$_3$ (1.6 g, 4.9 mmol). The reaction mixture was stirred at room temperature over night, then diluted with EtOAc, washed with water, dried and purified by silica gel column chromatography to give 31 (430 mg, 42%). $^1$H-NMR (400 MHz, CDCl$_3$): δ 7.15–7.40 (m, 5H), 5.40 (s, 2H), 2.84 (s, 3H), 2.75 (t, J=7.61 Hz, 2H), 1.80 (m, 2H), 0.99 (t, J=7.38 Hz, 3H).

Step 4: 5-benzyl-6-(1-bromo-propyl)-3-methyl-5H-isothiazolo[5,4-d]pyrimidin-4-one (32).

A mixture of 31 (430 mg, 1.44 mmol), bromine (345 mg, 2.16 mmol) and NaOAc (236 mg, 2.88 mmol) in acetic acid (10 mL) was heated at 40–45° C. for 14 h. The reaction mixture was poured into ice water, a yellow solid was collected by filtration. The crude product 32 was used in the next step without further purification. $^1$H-NMR (400 MHz, CDCl$_3$): δ 7.06–7.31 (m, 5H), 6.13 (d, J=16.41 Hz, 1H), 4.80 (d, J=16.41 Hz, 1H), 4.56 (t, J=7.26 Hz, 1H), 2.77 (s, 3H), 2.33 (m, 1H), 2.13 (m, 1H), 0.67 (t, J=7.27 Hz, 3H).

Step 5: {3-[1-(5-benzyl-3-methyl-4-oxo-4,5-dihydro-isothiazolo[5,4-d]pyrimidin-6-yl)-propylamino]-propyl}-carbamic acid tert-butyl ester (33).

A reaction mixture of 32 and N-Boc-1,3-diaminopropane (800 μl) in EtOH (10 ml) was heated at 90° C. for 14 h, then cooled to room temperature and purified by preparative HPLC to give 33 (350 mg) at the yield of 52% for two steps. 33 had an analytical HPLC retention time=3.03 min. (Column: YMC S5 Combiscreen 4.6×50 mm (4 min.); Solvent A=10% MeOH, 90% H$_2$O, 0.2% H$_3$PO$_4$; Solvent B=90% MeOH, 10% H$_2$O, 0.2% H$_3$PO$_4$) $^1$H-NMR (400 MHz, CDCl$_3$): δ 7.25–7.41 (m, 5H), 5.80 (d, J=16.41 Hz, 1H), 5.16 (d, J=16.41 Hz, 1H), 5.04 (brs, 1H), 4.66 (t, J=5.82 Hz, 1H), 3.11 (m, 2H), 2.89 (s, 3H), 2.72 (m, 1H), 2.57 (m, 1H), 2.02 (m, 2H), 2.74 (m, 2H), 1.43 (s, 9H), 0.84 (t, J=7.36 Hz, 3H).

Step 6: {3-[[1-(5-benzyl-3-methyl-4-oxo-4,5-dihydro-isothiazolo[5,4-d]pyrimidin-6-yl)-propyl]-(4-chloro-benzoyl)-amino]-propyl}-carbamic acid tert-butyl ester (34).

A reaction mixture of 33 (350 mg, 0.74 mmol), 4-chlorobenzoyl chloride (390 mg, 2.29 mmol) and Et$_3$N (412 μl, 2.96 mmol) in CH$_2$Cl$_2$ was stirred at room temperature for 14 h. The mixture was purified by silica gel column directly to give 34 (301 mg, 67%). 34 had an analytical HPLC retention time=4.41 min. (Column: YMC S5 Combiscreen 4.6×50 mm (4 min.); Solvent A=10% MeOH, 90% H$_2$O, 0.2% H$_3$PO$_4$; Solvent B=90% MeOH, 10% H$_2$O, 0.2% H$_3$PO$_4$).

Step 7: N-(3-amino-propyl)-N-[1-(5-benzyl-3-methyl-4-oxo-4,5-dihydro-isothiazolo[5,4-d]pyrimidin-6-yl)-propyl]-4-chloro-benzamide (35).

To a solution of 34 (62 mg, 0.14 mmol) in CH$_2$Cl$_2$ (8 mL) was added TFA (2 mL). The reaction mixture was stirred at room temperature for 1 h, concentrated in vacuo. The residue was purified by preparative HPLC to give 35 (58 mg, 76%) as a white solid. MS(ESI): 511 (M+H)$^+$.

Example 105

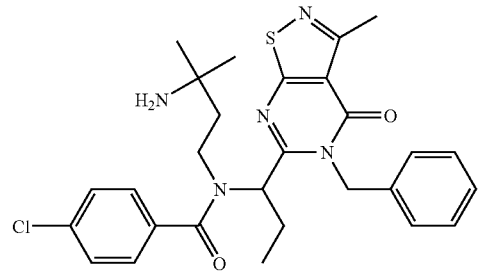

(±)-N-(3-Amino-3-methyl-butyl)-N-[1-(5-benzyl-3-methyl-4-oxo-4,5-dihydroisothiazolo[5,4-d]pyrimidin-6-yl)-propyl]-4-chloro-benzamide (39)

Step 1: 6-(1-amino-propyl)-5-benzyl-3-methyl-5H-isothiazolo[5,4-d]pyrimidin-4-one (36).

A mixture of 32 (160 mg, 0.42 mmol) and 7N ammonia in MeOH (7.5 mL) was heated in a sealed tube at 120° C. for 2 h, and cooled to room temperature. Solvent was removed to give a yellow solid 36 (136 mg, 100%), which was used without further purification. $^1$H-NMR (400 MHz, CDCl$_3$): δ 7.07–7.28 (m, 5H), 5.39 (s 2H), 4.23 (brs, 2H), 4.15 (t, J=5.99 Hz, 1H), 2.72 (s, 3H), 1.46–1.66 (m, 2H), 0.75 (t, J=7.37 Hz, 3H).

Step 2: 2,4,4-Trimethyl-5,6-dihydro-4H-[1,3]oxazine.

Acetonitrile(22.6 g, 0.25 mol) was dripped into concentrated H$_2$SO$_4$(150 mL) at 0° C. Upon complete addition of acetonitrile, 3-methyl-butane-1,3-diol(22.6 g, 0.55 mol) was dripped into the reaction vessel over 0.5 h maintaining the reaction temperature at or below 5° C. The resulting mixture was stirred for 1.5 h at 5° C. and then poured onto crushed ice. When the ice melted, the aqueous layer was extracted with ether (2×250 mL). The organic was discarded and the aqueous was treated with 40% NaOH to pH 12. The basic aqueous was extracted with ether. The organic layer was washed with brine and dried (MgSO$_4$). The ether was removed in vacuo at 25° C. affording the desired product as a colorless oil (25.4 g, 50%); $^1$H NMR (DMSO-d6) δ 4.04 (t, J=6 Hz, 2H), δ 1.72 (s, 3H), δ 1.61 (t, J=6 Hz, 2H), δ 1.07 (s, 6H).

Step 3: 3-Amino-3-methyl-butan-1-ol.

2,4,4-Trimethyl-5,6-dihydro-4H-[1,3]oxazine(25.15 g, 0.20 mol) was dissolved in 6N NaOH(65 mL, 0.40 mol) and stirred at 80° C. for 18 h. The resulting mixture was cooled to 25° C. and extracted with CH$_2$Cl$_2$(3×100 mL). The organic was dried(MgSO$_4$) and concentrated to afford the desired material as a colorless oil(5.1 g, 20%); $^1$H NMR (DMSO-d6) δ 3.55 (t, J=7 Hz, 2H), δ 1.47 (t, J=7 Hz, 2H), δ 1.03 (s, 6H).

Step 4: (3-Hydroxy-1,1-dimethyl-propyl)-carbamic acid tert-butyl ester.

3-Amino-3-methyl-butan-1-ol(5.0 g, 0.04 mol) was dissolved in 150 mL CH$_2$Cl$_2$ and treated with di-tert-butyl dicarbonate(11.12 g, 0.05 mol). The resulting mixture was stirred for 18 h at 25° C. The mixture was concentrated to the desired material as an amber oil(9.8 g, 100%); $^1$H NMR (DMSO-d6) δ 3.55 (s, 1H), δ 4.43 (t, J=5 Hz, 1H), δ 3.46 (m, 2H), δ 1.71 (t, J=7 Hz, 2H), δ 1.37(s, 9H), δ 1.12(s, 6H).

Step 5: (1,1-Dimethyl-3-oxo-propyl)-carbamic acid tert-butyl ester.

(3-Hydroxy-1,1-dimethyl-propyl)-carbamic acid tert-butyl ester(9.8 g, 0.048 mol)was dissolved in DMSO(160 mL). The solution was treated with Et$_3$N(20.2 mL, 0.145 mol) followed by a solution of pyridine sufurtrioxide complex (23.15 g, 0.145 mol) in DMSO(160 mL). Upon complete addition, the solution was stirred for 1 h at 25° C. The mixture was diluted with brine and extracted with Et$_2$O(3× 125 mL). The organic phase was washed with 10% citric acid(aq), saturated NaHCO$_3$ and brine. The organic was dried(MgSO$_4$) and concentrated to the desired material as a yellow oil(8.3 g, 56%); $^1$H NMR (DMSO-d6) δ 9.67 (t, J=3 Hz, 1H), δ 2.66 (s, 2H), δ 1.37 (s, 9H), δ 1.28 (s, 6H).

Step 6: {3-[1-(5-benzyl-3-methyl-4-oxo-4,5-dihydro-isothiazolo[5,4-d]pyrimidin-6-yl)-propylamino]-1,1-dimethyl-propyl}-carbamic acid tert-butyl ester (37).

To a solution of 36 (136 mg, 0.433 mmol) in MeOH (5 ml) was added (1,1-dimethyl-3-oxo-propyl)-carbamic acid tert-butyl ester(105 mg, 0.522 mmol) followed by NaBH(OAc)$_3$ (138 mg, 0.65 mmol). The reaction mixture was stirred at room temperature overnight, quenched with water. Solvent was removed in vacuo, the residue was purified by preparative HPLC to give 37 (86 mg) at the yield of 41% for the two steps. $^1$H-NMR (500 MHz, CDCl$_3$): δ 7.23–7.39 (m, 5H), 5.89 (d, J=16.0 Hz, 1H), 5.01 (d, J=16.0 Hz, 1H), 4.66 (t, J=5.77 Hz, 1H), 4.43 (brs, 1H), 2.86 (s, 3H), 2.45 (m, 2H), 2.11 (m, 1H), 1.96 (m, 2H), 1.74 (m, 1H), 1.30 (s, 9H), 1.13 (s, 3H), 1.01 (s, 3H), 0.88 (t, J=7.42 Hz, 3H).

Step 7: {3-[[1-(5-benzyl-3-methyl-4-oxo-4,5-dihydro-isothiazolo[5,4-d]pyrimidin-6-yl)-propyl]-(4-chloro-benzoyl)-amino]-1,1-dimethyl-propyl}-carbamic acid tert-butyl ester (38).

Compound 38 was prepared from 37 by a route analogous to that used for the preparation of Compound 34. $^1$H-NMR (500 MHz, CDCl$_3$): δ 7.08–7.33 (m, 9H), 5.92 (d, J=15.40 Hz, 1H), 5.84 (brs, 1H), 5.07 (d, J=15.95 Hz, 1H), 3.26 (m, 2H), 2.76 (s, 3H), 1.95 (m, 1H), 1.81 (m, 1H), 1.66 (m, 1H), 1.08 (m, 1H), 0.84 (s, 3H), 0.68 (s, 3H), 0.57(brs, 3H).

Step 8: N-(3-amino-3-methyl-butyl)-N-[1-(5-benzyl-3-methyl-4-oxo-4,5-dihydroisothiazolo[5,4-d]pyrimidin-6-yl)-propyl]-4-chloro-benzamide (39).

Compound 39 was prepared from 38 by a route analogous to that used for the preparation of Compound 35. MS(ESI): 538 (M+1)$^+$.

What is claimed is:

1. A compound of formula I or II:

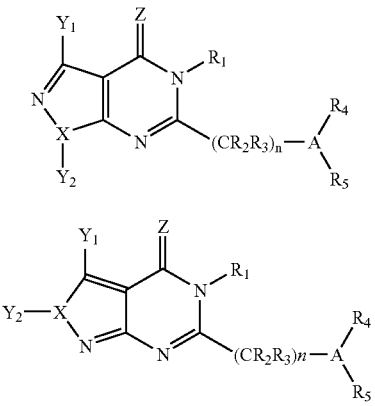

wherein:

X is O, or S

Y$_1$ is H, alkyl, substituted alkyl, aryl, substituted aryl, cycloalkyl or substituted cycloalkyl;

Z is O or S;

R$_1$ is H, or alkyl,

R$_2$ and R$_3$ are, independently, H alkyl, cycloalkyl or halogen or R$_2$ and R$_3$ may be taken together to form a C$_3$ to C$_7$ cycloalkyl;

n is 1 or 2;

A is N;

R$_4$ is H, C(=O)R$_9$, C(=O)OR$_{10}$, C(=O)NR$_{11}$R$_{12}$, or S(O)$_2$R$_{13}$,

R$_9$, R$_{10}$, R$_{11}$, R$_{12}$, R$_{13}$ are independently H, alkyl optionally substituted with alkoxy, alkyl, halo, alkylthio, hydroxyl, cyano, carboxy, amino, amido, carbamoyl, urea or thiol; cycloalkyl, optionally substituted with halogen, alkyl, alkoxy, hydroxyl, amino, amido, carbamoyl, urea, nitro, cyano, thiol; o, aryl, optionally substituted with alkyl, alkcoxy, halo, cyano, hydroxyl, carboxy, carbamoyl, alkyoxycarbonyl, nitro, alkenyloxy, trifluoromethyl, amino, cycloalkyl, aryl, heteroaryl, cyano, alkyl, sulfoxyl, sulfonyl, or thiol; or heteroaryl, optionally substituted with halo, alkyl, alkenyl, alkynyl, aryl, nitro, cyano, hydroxyl, alkoxy, thioalkyl, carboxy, carbonyl, phenyl, benzyl, phenylethyl, phenoxy, phenylthio, cycloalkyl, heterocycloalkyl, heteroaryl, amion, amido, heteroaryl, amino or amido; and $R_5$ is H, or alkyl, optionally substituted with alkoxy, alkyl, halo, alkylthio, hydroxyl, cyano, carboxy, amino, amido, carbamoyl, urea or thiol.

2. The compound of claim 1 wherein $R_1$ is aralkyl.
3. The compound of claim 1 wherein $R_1$ is benzyl.
4. The compound of claim 1 wherein $R_2$ is alkyl.
5. The compound of claim 4 wherein $R_2$ is ethyl.
6. The compound of claim 1 wherein $R_3$ is H.
7. The compound of claim 1 wherein $R_4$ is H, —(C=O)$R_9$, or $SO_2R_{13}$.
8. The compound of claim 7 wherein $R_9$ is phenyl optionally substituted with halogen, alkyl, —$CF_3$, alkoxy, nitro, sulfonyl, or amido.
9. The compound of claim 1 wherein $R_5$ is alkyl optionally substituted with amino, cyano, alkoxy, phenyl, cyano, or amido.
10. The compound of claim 9 wherein $R_5$ is ethyl, propyl, or butyl.
11. The compound of claim 1 wherein $Y_1$ is alkyl, or aryl.
12. The compound of claim 1 wherein X is O, or S; Z is O; $R_1$ is aralkyl; $R_2$ is alkyl; $R_3$ is H; $R_4$ is H, —(C=O)$R_9$, or $SO_2R_{13}$; $R_5$ is alkyl optionally substituted with alkoxy, alkyl, halo, alkylthio, hydroxyl, cyano, carboxy, amino, amido, carbamoyl, urea or thiol; and $Y_1$ is alkyl, substituted alkyl, aryl or substituted aryl.
13. The compound of claim 1 wherein $R_5$ is cyanoethyl, propionamide or propylamine.
14. A compound selected from the group consisting of
(±)-N-(3-Amino-propyl)-N-[1-(5-benzyl-3-methyl-4-oxo-4,5-dihydro-isoxazolo[5,4-d]pyrimidin-6-yl)-propyl]-4-methyl-benzamide
(±)-3-[1-(5-Benzyl-3-methyl-4-oxo-4,5-dihydro-isoxazolo[5,4-d]pyrimidin-6-yl)-propylamino]-propionitrile
(±)-N-[1-(5-Benzyl-3-methyl-4-oxo-4,5-dihydro-isoxazolo[5,4-d]pyrimidin-6-yl)-propyl]-4-methyl-N-(3-morpholin-4-yl-propyl)-benzamide
(±)-N-[1-(5-Benzyl-3-methyl-4-oxo-4,5-dihydro-isoxazolo[5,4-d]pyrimidin-6-yl)-propyl]-N-(3-methoxy-propyl)-4-methyl-benzamide
(±)-N-[1-(5-Benzyl-3-methyl-4-oxo-4,5-dihydro-isoxazolo[5,4-d]pyrimidin-6-yl)-propyl]-4-methyl-N-phenethyl-benzamide
(±)-N-[1-(5-Benzyl-3-methyl-4-oxo-4,5-dihydro-isoxazolo[5,4-d]pyrimidin-6-yl)-propyl]-N-(2-cyano-ethyl)-4-methyl-benzamide
(±)-N-[1-(5-Benzyl-3-methyl-4-oxo-4,5-dihydro-isoxazolo[5,4-d]pyrimidin-6-yl)-propyl]-N-(2-carbamoyl-ethyl)-4-methyl-benzamide
(±)-N-[1-(5-Benzyl-3-methyl-4-oxo-4,5-dihydro-isoxazolo[5,4-d]pyrimidin-6-yl)-propyl]-N-(3-imidazol-1-yl-propyl)-4-methyl-benzamide
(±)-N-[1-(5-Benzyl-3-methyl-4-oxo-4,5-dihydro-isoxazolo[5,4-d]pyrimidin-6-yl)-propyl]-N-(2-cyano-ethyl)-2-methoxy-benzamide
(±)-N-[1-(5-Benzyl-3-methyl-4-oxo-4,5-dihydro-isoxazolo[5,4-d]pyrimidin-6-yl)-propyl]-N-(2-cyano-ethyl)-benzamide
(±)-N-[1-(5-Benzyl-3-methyl-4-oxo-4,5-dihydro-isoxazolo[5,4-d]pyrimidin-6-yl)-propyl]-N-(2-cyano-ethyl)-3-fluoro-benzamide
(±)-N-[1-(5-Benzyl-3-methyl-4-oxo-4,5-dihydro-isoxazolo[5,4-d]pyrimidin-6-yl)-propyl]-3,4-dichloro-N-(2-cyano-ethyl)-benzamide
(±)-N-[1-(5-Benzyl-3-methyl-4-oxo-4,5-dihydro-isoxazolo[5,4-d]pyrimidin-6-yl)-propyl]-N-(2-cyano-ethyl)-2-methyl-benzamide
(±)-N-[1-(5-Benzyl-3-methyl-4-oxo-4,5-dihydro-isoxazolo[5,4-d]pyrimidin-6-yl)-propyl]-N-(2-cyano-ethyl)-4-fluoro-benzamide
(±)-N-[1-(5-Benzyl-3-methyl-4-oxo-4,5-dihydro-isoxazolo[5,4-d]pyrimidin-6-yl)-propyl]-4-chloro-N-(2-cyano-ethyl)-benzamide
(±)-N-[1-(5-Benzyl-3-methyl-4-oxo-4,5-dihydro-isoxazolo[5,4-d]pyrimidin-6-yl)-propyl]4-tert-butyl-N-(2-cyano-ethyl)-benzamide
(±)-N-[1-(5-Benzyl-3-methyl-4-oxo-4,5-dihydro-isoxazolo[5,4-d]pyrimidin-6-yl)-propyl]-4-cyano-N-(2-cyano-ethyl)-benzamide
(±)-N-[1-(5-Benzyl-3-methyl-4-oxo-4,5-dihydro-isoxazolo[5,4-d]pyrimidin-6-yl)-propyl]-N-(2-cyano-ethyl)-isonicotinamide
(±)-N-[1-(5-Benzyl-3-methyl-4-oxo-4,5-dihydro-isoxazolo[5,4-d]pyrimidin-6-yl)-propyl]-N-(2-cyano-ethyl)-nicotinamide
(±)-N-[1-(5-Benzyl-3-methyl-4-oxo-4,5-dihydro-isoxazolo[5,4-d]pyrimidin-6-yl)-propyl]-N-(2-cyano-ethyl)-benzenesulfonamide
(±)-3-{[1-(5-Benzyl-3-methyl-4-oxo-4,5-dihydro-isoxazolo[5,4-d]pyrimidin-6-yl)-propyl]-[2-(4-chloro-phenyl)-2-oxo-ethyl]-amino}-propionitrile
(±)-N-[1-(5-Benzyl-3-methyl-4-oxo-4,5-dihydro-isoxazolo[5,4-d]pyrimidin-6-yl)-propyl]-4-chloro-N-(2-cyano-ethyl)-benzenesulfonamide
(±)-N-[1-(5-Benzyl-3-methyl-4-oxo-4,5-dihydro-isoxazolo[5,4-d]pyrimidin-6-yl)-propyl]-N-(2-cyano-ethyl)-4-methoxy-benzenesulfonamide
(±)-N-[1-(5-Benzyl-3-methyl-4-oxo-4,5-dihydro-isoxazolo[5,4-d]pyrimidin-6-yl)-propyl]-4-tert-butyl-N-(2-cyano-ethyl)-benzenesulfonamide
(±)-N-[1-(5-Benzyl-3-methyl-4-oxo-4,5-dihydro-isoxazolo[5,4-d]pyrimidin-6-yl)-propyl]-N-(2-cyano-ethyl)-3-niethyl-benzenesulfonamide
(±)-N-[1-(5-Benzyl-3-methyl-4-oxo-4,5-dihydro-isoxazolo[5,4-d]pyrimidin-6-yl)-propyl]-N-(2-cyano-ethyl)-4-trifluoromethyl-benzamide
(±)-Quinoline-2-carboxylic acid [1-(5-benzyl-3-methyl-4-oxo-4,5-dihydro-isoxazolol[5,4-d]pyrimidin-6-yl)-propyl]-(2-cyano-ethyl)-amide
(±)-N-[1-(5-Benzyl-3-methyl-4-oxo-4,5-dihydro-isoxazolol[5,4-d]pyrimidin-6-yl)-propyl]-N-(2-cyano-ethyl)-4-methyl-benzenesulfonamide
(±)-5-Methyl-isoxazole-3-carboxylic acid [1-(5-benzyl-3-methyl-4-oxo-4,5-dihydro-isoxazolo[5,4-d]pyrimidin-6-yl)-propyl]-(2-cyano-ethyl)-amide
(±)-Cyclobutanecarboxylic acid [1-(5-benzyl-3-methyl-4-oxo-4,5-dihydro-isoxazolo[5,4-d]pyrimidin-6-yl)-propyl]-(2-cyano-ethyl)-amide
(±)-N-[1-(5-Benzyl-3-methyl-4-oxo-4,5-dihydro-isoxazolo[5,4-d]pyrimidin-6-yl)-propyl]-N-(2-cyano-ethyl)-3-methyl-butyramide
(±)-Cyclohexanecarboxylic acid [1-(5-benzyl-3-methyl-4-oxo-4,5-dihydro-isoxazolol[5,4-d]pyrimidin-6-yl)-propyl]-(2-cyano-ethyl)-amide
(±)-N-[1-(5-Benzyl-3-methyl-4-oxo-4,5-dihydro-isoxazolo[5,4-d]pyrimidin-6-yl)-propyl]-(2-cyano-ethyl)-acetamide (±)-N-[1-(5-Benzyl-3-methyl-4-oxo-4,5-dihydro-isoxazolo[5,4-d]pyrimidin-6-yl)-propyl]-(2-cyano-ethyl)-2-methoxy-acetamide (±)-2,2,2-Trifluoro-ethanesulfonic acid [1-(5-benzyl-3-methyl-4-oxo-4,5-dihydro-isoxazolo[5,4-d]pyrimidin-6-yl)-propyl]-(2-cyano-ethyl)-amide (±)-Propane-1-sulfonic acid [1-(5-benzyl-3-methyl-4-oxo-4,5-dihydro-isoxazolo[5,4-d]pyrimidin-6-yl)-propyl]-(2-cyano-ethyl)-amide (±)-3-[1-(5-Benzyl-3-methyl-4-oxo-4,5-dihydro-isoxazolo[5,4-d]pyrimidin-6-yl)-propylamino]-propionamide (±)-N-[1-(5-Benzyl-3-methyl-4-oxo-4,5-dihydro-isoxazolo[5,4-d]pyrimidin-6-yl)-propyl]-N-(2-carbamoyl-ethyl)-benzamide (±)-N-[1-(5-Benzyl-3-methyl-4-oxo-4,5-dihydro-isoxazolo[5,4-d]pyrimidin-6-yl)-propyl]-N-(2-carbamoyl-ethyl)-3-fluoro-benzamide (±)-N-[1-(5-Benzyl-3-methyl-4-oxo-4,5-dihydro-isoxazolo[5,4-d]pyrimidin-6-yl)-propyl]-N-(2-carbamoyl-ethyl)-3,4-dichloro-benzamide (±)-N-[1-(5-Benzyl-3-methyl-4-oxo-4,5-dihydro-isoxazolo[5,4-d]pyrimidin-6-yl)-propyl]-N-(2-carbamoyl-ethyl)-4-methoxy-benzamide (±)-N-[1-(5-Benzyl-3-methyl-4-oxo-4,5-dihydro-isoxazolo[5,4-d]pyrimidin-6-yl)-propyl]-N-(2-carbamoyl-ethyl)-2-methyl-benzamide (±)-N-[1-(5-Benzyl-3-methyl-4-oxo-4,5-dihydro-isoxazolo[5,4-d]pyrimidin-6-yl)-propyl]-N-(2-carbamoyl-ethyl)-3-methyl-benzamide (±)-N-[1-(5-Benzyl-3-methyl-4-oxo-4,5-dihydro-isoxazolo[5,4-d]pyrimidin-6-yl)-propyl]-N-(2-carbamoyl-ethyl)-4-fluoro-benzamide (±)-N-[1-(5-Benzyl-3-methyl-4-oxo-4,5-dihydro-isoxazolo[5,4-d]pyrimidin-6-yl)-propyl]-N-(2-carbamoyl-ethyl)-4-chloro-benzamide (±)-N-[1-(5-Benzyl-3-methyl-4-oxo-4,5-dihydro-isoxazolo[5,4-d]pyrimidin-6-yl)-propyl]-N-(2-carbamoyl-ethyl)-3-trifluoromethyl-benzamde (±)-N-[1-(5-Benzyl-3-methyl-4-oxo-4,5-dihydro-isoxazolo[5,4-d]pyrimidin-6-yl)-propyl]-4-tert-butyl-N-(2-carbamoyl-ethyl)-benzamide (±)-N-[1-(5-Benzyl-3-methyl-4-oxo-4,5-dihydro-isoxazolo[5,4-d]pyrimidin-6-yl)-propyl]-N-(2-carbamoyl-ethyl)-4-cyano-benzamide (±)-N-[1-(5-Benzyl-3-methyl-4-oxo-4,5-dihydro-isoxazolol[5,4-d]pyrimidin-6-yl)-propyl]-N-(2-carbamoyl-ethyl)-3-cyano-benzamide (±)-N-[1-(5-Benzyl-3-methyl-4-oxo-4,5-dihydro-isoxazolo[5,4-d]pyrimidin-6-yl)-propyl]-butyl-N-(2-carbamoyl-ethyl)-nicotinamide (±)-3-{[1-(5-Benzyl-3-methyl-4-oxo-4,5-dihydro-isoxazolo[5,4-d]pyrimidin-6-yl)-propyl]-[2-(4-chloro-phenyl)-2-oxo-ethyl]-amino}-propionamide (±)-3-[[1-(5-Benzyl-3-methyl-4-oxo-4,5-dihydro-isoxazolo[5,4-d]pyrimidin-6-yl)propyl]-(toluene-3-sulfonyl)-amino]-propionamide (±)-N-[1-(5-Benzyl-3-methyl-4-oxo-4,5-dihydro-isoxazolo[5,4-d]pyrimidin-6-yl)-propyl]-butyl-N-(2-carbamoyl-ethyl)-4-trifluoromethyl-benzamide (±)-Quinoline-2-carboxylic acid [1-(5-benzyl-3-methyl-4-oxo-4,5-dihydro-isoxazolo[5,4-d]pyrimidin-6-yl)-propyl]-butyl-N-(2-carbamoyl-ethyl)-amide (±)-3-[[1-(5-Benzyl-3-methyl-4-oxo-4,5-dihydro-isoxazolo[5,4-d]pyrimidin-6-yl)-propyl]-(1-methyl 1H-imidazole-4-sulfonyl)-amino]-propionamide (±)-5-methyl-isoxazole-3-carboxylic acid [1-(5-Benzyl-3-methyl-4-oxo-4,5-dihydro-isoxazolo[5,4-d]pyrimidin-6-yl)-propyl]-(1-methyl-1H-imidazole-4-sulfonyl)-amino]-amide (±)-Cyclobutanecarboxylic acid [1-(5-benzyl-3-methyl-4-oxo-4,5-dihydro-isoxazolo[5,4-d]pyrimidin-6-yl)-propyl]-amide (±)-N-[1-(5-Benzyl-3-methyl-4-oxo-4,5-dihydro-isoxazolo[5,4-d]pyrimidin-6-yl)-propyl]-butyl-N-(2-carbaxnoyl-ethyl)-isobutyramide (±)-N-[1-(5-Benzyl-3-methyl-4-oxo-4,5-dihydro-isoxazolo[5,4-d]pyrimidin-6-yl)-propyl]-butyl-N-(2-carbamoyl-ethyl)-3-methyl-butyramide (±)-3-{Acetyl-[1-(5-benzyl-3-methyl-4-oxo-4,5-dihydro-isoxazolo[5,4-d]pyrimidin-6-yl)-propyl]-amino}-propionamide (±)-3-[[1-(5-Benzyl-3-methyl-4-oxo-4,5-dihydro-isoxazolo[5,4-d]pyrimidin-6-yl)-propyl]-(2-methoxy-aeetyl)-amino]-propionamide (±)-3-[[1-(5-Benzyl-3-methyl-4-oxo-4,5-dihydro-isoxazolo[5,4-d]pyrimidin-6-yl)-propyl]-(2,2,2-trifluoro-ethanesulfonyl)-amino]-propionamide (±)-N-[1-(5-Benzyl-3-methyl-4-oxo-4,5-dihydro-isoxazolo[5,4-d]pyrimidin-6-yl)-propyl]-4-bromo-N-(2-caibamoyl-ethyl)-benzamide (±)-N-(3-Amino-propyl)-N-[1-(5-benzyl-3-methyl-4-oxo-4,5-dihydro-isoxazolo[5,4-d]pyrimidin-6-yl)-propyl]-2-methoxy-benzamide (±)-N-(3-Amino-propyl)-N-[1-(5-benzyl-3-methyl-4-oxo-4,5-dihydro-isoxazolo[5,4-d]pyrimidin-6-yl)-propyl]-benzamide (±)-N-(3-Amino-propyl)-N-[1-(5-benzyl-3-methyl-4-oxo-4,5-dihydro-isoxazolo[5,4-d]pyrimidin-6-yl)-propyl]-3-fluoro-benzamide (±)-N-(3-Amino-propyl)-N-[1-(5-benzyl-3-methyl-4-oxo-4,5-dihydro-isoxazolo[5,4-d]pyrimidin-6-yl)-propyl]-3,4-dichloro-benzamide (±)-N-(3-Amino-propyl)-N-[1-(5-benzyl-3-methyl-4-oxo-4,5-dihydro-isoxazolo[5,4-d]pyrimidin-6-yl)-propyl]-3-propyl-benzamide (±)-N-(3-Amino-propyl)-N-[1-(5-benzyl-3-methyl-4-oxo-4,5-dihydro-isoxazolo[5,4-d]pyrimidin-6-yl)-propyl]-2-methyl-benzamide (±)-N-(3-Amino-propyl)-N-[1-(5-benzyl-3-methyl-4-oxo-4,5-dihydro-isoxazolo[5,4-d]pyrimidin-6-yl)-propyl]-3-methyl-benzamide (±)-N-(3-Amino-propyl)-N-[1-(5-benzy-1-3-methyl-4-oxo-4,5-dihydro-isoxazo[5,4-d]pyrimidin-6-yl)-propyl]-4-chloro-benzamide (±)-N-(3-Amino-propyl)-N-[1-(5-benzyl-3-methyl-4-oxo-4,5-dihydro-isoxazolo[5,4-d]pyrimidin-6-yl)-propyl]-isonicotinamide (±)-N-(3-Amino-propyl)-N-[1-(5-benzyl-3-methyl-4-oxo-4,5-dihydro-isoxazolo[5,4-d]pyrimidin-6-yl)-propyl]-benzenesulfonamide (±)-Biphenyl-4-carboxylic acid (3-amino-propyl)-[1-(5-benzyl-3-methyl-4-oxo-4,5-dihydro-isoxazolo[5,4-d]pyrimidin-6-yl)-propyl]-amide (±)-N-(3Amino-propyl)-N-[1-(5-benzyl-3-methyl-4-oxo-4,5-dihydro-isoxazolo[5,4-d]pyrimidin-6-yl)-propyl]-4-ethyl-benzamide (±)-6-(1-{(3-Amino-propyl)-[2-(4-chloro-phenyl)-2-oxo-ethyl]-amino}-propyl)-5-benzyl-3-methyl-5H-isoxazolo[5,4-d]pyrimidin-4-one (±)-N-(3-Amino-propyl)-N-[1-(5-benzyl-3-methyl-4-oxo-4,5-dihydro-isoxazolo[5,4-d]pyrimidin-6-yl)-propyl]-4-trifluoromethoxy-benzamide (±)-N-(3-Amino-propyl)-N-[1-(5-benzyl-3-methyl-4-oxo-4,5-dihydro-isoxazalo[5,4-d]pyrimidin-6-yl)-propyl]-4-chloro-benzenesulfonamide (±)-N-(3-Amino-propyl)-N-[1-(5-benzyl-3-methyl-4-oxo-4,5-dihydro-isoxazolo[5,4-d]pyrimidin-6-yl)-propyl]-4-nitro-benzamide (±)-N-(3-Amino-propyl)-N-[1-(5-benzyl-3-methyl-4-oxo-4,5-dihydro-isoxazolo[5,4-d]pyrimidin-6-yl)-propyl]-4-tert-butyl-benzenesulfonamide (±)-N-(3-Amino-propyl)-N-[1-(5-benzyl-3-methyl-4-oxo-4,5-dihydro-isoxazolo[5,4-d]pyrimidin-6-yl)-propyl]-3-methyl-benzenesulfonamide (±)-Quinoline-2-carboxylic acid (3-amino-propyl)-[1-(5-benzyl-3-methyl-4-oxo-4,5-dihydro-isoxazolo[5,4-d]pyrimidin-6-yl)-propyl]-amide (±)-N-(3-Amino-propyl)-N-[1-(5-benzyl-3-methyl-4-oxo-4,5-dihydro-isoxazolo[5,4-]pyrimidin-6-yl)-propyl]-4-methyl-benzenesulfonamide (±)-4-{(3-Amino-propyl)-N-[1-(5-benzyl-3-methyl-4-oxo-4,5-dihydro-isoxazolo[5,4-d]pyrimidin-6-yl)-propyl]-carbamoyl}-benzenesulfonyl fluoride (±)-5-methyl-isoxazole-3-carboxylic acid (3-amino-propyl)-[1-(5-benzyl-3-methyl-4-oxo-4,5-dihydro-isoxazolo[5,4-d]pyrimidin-6-yl)-propyl]-amide (±)-Cyclobutanecarboxylic acid (3-amino-propyl)-[1-(5-benzyl-3-methyl-4-oxo-4,5-dihydro-isoxazolo[5,4-d]pyrimidin-6-yl)-propyl]-amide (±)-N-(3-Amino-propyl)-N-[1-(5-benzyl-3-methyl-4-oxo-4,5-dihydro-isaxazolol[5,4-d]pyrimidin-6-yl)-propyl]-isobutyramide (±)-N-(3-Amino-propyl)-N-[1-(5-benzyl-3-methyl-4-oxo-4,5-dihydro-isoxazolo[5,4-d]pyrimidin-6-yl)-propyl]-3-methyl-butyramide (±)-N-(3-Amino-propyl)-N-[1-(5-benzyl-3-methyl-4-oxo-4,5-dihydro-isoxazolo[5,4-d]pyrimidin-6-yl)-acetamide (±)-N-(3-Amino-propyl)-N-[1-(5-benzyl-3-methyl-4-oxo-4,5-dihydro-isoxazolo[5,4-d]pyrimidin-6-yl)-propyl]-2-methoxy-acetamide (±)-N-(3-Amino-propyl)-N-[1-(5-benzyl-3-methyl-4-oxo-4,5-dihydro-isoxazolo[5,4-d]pyrimidin-6-yl)-propyl]-4-trifluoromethylsulfanyl-benzenesulfonamide (±)-2,2,2-Trifluoro-ethanesulfonic acid (3-Amino-propyl)-[1-(5-benzyl-3-methyl-4-oxo-4,5-dihydro-isoxazolo[5,4-d]pyrimidin-6-yl)-amide (±)-4-Acetylamino-N-(3-amino-propyl)-N-[1-(5-benzyl-3-methyl-4-oxo-4,5-dihydro-isoxazolo[5,4-d]pyrimidin-6-yl)-benzamide (±)-4-{(3-Amino-propyl)-[1-(5-benzyl-3-methyl-4-oxo-4,5-dihydro-isoxazolo[5,4-d]pyrimidin-6-yl)-propyl]-sulfamoyl}-benzoic acid methyl ester (±)-N-(3-Amino-propyl)-N-[1-(5-benzyl-3-methyl-4-oxo-4,5-dihydro-isoxazolo[5,4-d]pyrimidin-6-yl)-propyl]-4-bromo-benzamide (±)-N-(3-Amino-propyl)-N-[1-(5-benzyl-4-oxo-3-trifluoromethyl-4,5-dihydro-isoxazolo[5,4-d]pyrimidin-6-yl)-propyl]-4-bromo-benzamide (±)-N-(3-Amino-propyl)-N-[1-(5-benzyl-4-oxo-3-phenyl-4,5-dihydro-isoxazolo[5,4-d]pyrimidin-6-yl)-propyl]-4-methyl-benzamide (±)-N-(3-Aminopropyl)-N-[1-(5-benzyl-3-isopropyl-4-oxo-4,5-dihydro-isoxazolo[5,4-d]pyrimidin-6-yl)-propyl]-4-methylbenzamide Hydrochloride (±)-N-(3-Aminopropyl)-N-{1-[5-(4-chlorobenzyl)-3-isopropyl-4-oxo-4,5-dihydroisoxazolo[5,4-d]pyrimidin-6-yl]-propyl}-4-methylbenzamide Hydrochloride (±)-N-(3-Amino-propyl)-N-[1-(5-benzyl-3-methyl-4-oxo-4,5-dihydro-isothiazolo[5,4-d]pyrimidin-6-yl)-propyl]-4-chloro-benzamide; and (±)-N-(3-Amino-3-methyl-butyl)-N-[1-(5-benzyl-3-methyl-4-oxo-4,5-dihydroisothiazolo[5,4-d]pyrimidin-6-yl)-propyl]-4-chloro-benzamide.

15. A compound having the formula:

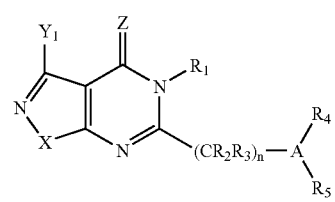

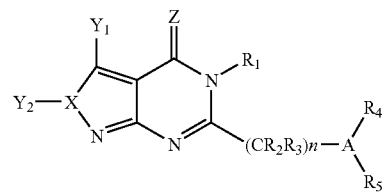

wherein $Y_1$ is H or methyl;

$R_1$ is benzyl;

$R_2$ is ethyl;

$R_3$ is H;

$R_4$ is $C(O)R_9$;

$R_5$ is alkyl substituted with amino;

$R_9$ is phenyl optionally substituted with alkyl, halo, or methoxy, n is 1; and X is S or O.

16. A compound having the formula (±)-N-(3-Aminopropyl)-N-[1-(5-benzyl-3-methyl-4-oxo-4,5-dihydroisothiazolo[5,4-d]pyrimidin-6-yl)-propyl]-4-chloro-benzamide.

* * * * *